(12) United States Patent
Spero et al.

(10) Patent No.: US 10,900,896 B2
(45) Date of Patent: Jan. 26, 2021

(54) FLOW CELLS UTILIZING SURFACE-ATTACHED STRUCTURES, AND RELATED SYSTEMS AND METHODS

(71) Applicant: REDBUD LABS, INC., RTP, NC (US)

(72) Inventors: Richard Chasen Spero, Chapel Hill, NC (US); Jay Kenneth Fisher, Durham, NC (US); Richard Superfine, Chapel Hill, NC (US)

(73) Assignee: REDBUD LABS, INC., Research Triangle Park, NC (US)

( * ) Notice: Subject to any disclaimer, the term of this patent is extended or adjusted under 35 U.S.C. 154(b) by 196 days.

(21) Appl. No.: 15/761,109

(22) PCT Filed: Sep. 19, 2016

(86) PCT No.: PCT/US2016/052463
§ 371 (c)(1),
(2) Date: Mar. 18, 2018

(87) PCT Pub. No.: WO2017/049279
PCT Pub. Date: Mar. 23, 2017

(65) Prior Publication Data
US 2018/0266951 A1    Sep. 20, 2018

Related U.S. Application Data

(60) Provisional application No. 62/347,046, filed on Jun. 7, 2016, provisional application No. 62/220,906, filed on Sep. 18, 2015.

(51) Int. Cl.
*B01L 3/00* (2006.01)
*G01N 21/63* (2006.01)
(Continued)

(52) U.S. Cl.
CPC ......... *G01N 21/631* (2013.01); *B01F 5/0617* (2013.01); *B01F 13/0059* (2013.01);
(Continued)

(58) Field of Classification Search
CPC ...... G01N 21/631; G01N 21/63; G01N 21/62; G01N 21/00; B01F 5/0617; B01F 5/0616;
(Continued)

(56) References Cited

U.S. PATENT DOCUMENTS 8,304,230 B2 * 11/2012 Toner ................ B01L 3/502746
435/288.5
8,435,465 B2 * 5/2013 Sundaram .............. C12M 47/06
422/554
(Continued)

*Primary Examiner* — Christine T Mui
(74) *Attorney, Agent, or Firm* — E. Eric Mills; Nexsen Pruet, PLLC

(57) ABSTRACT

A flow cell is provided that includes surface-attached structures in a chamber. The structures are movable in response to a magnetic or electric field. A target extraction or isolation system includes the flow cell and a driver configured for applying a magnetic or electric field to the interior of the flow cell to actuate movement of the structures. The flow cell may be utilized to extract or isolate a target from a sample flowing through the flow cell. Further, a microfluidic system is provided that includes surface-attached structures and a microarray, wherein actuated motion of the surface-attached structures is used to enhance flow, circulation, and/or mixing action for analyte capture on the microarray.

24 Claims, 20 Drawing Sheets

(51) Int. Cl.
*G01N 21/05* (2006.01)
*G01N 33/543* (2006.01)
*B01F 5/06* (2006.01)
*B01F 13/00* (2006.01)
*B01F 5/00* (2006.01)

(52) U.S. Cl.
CPC ...... *B01F 13/0091* (2013.01); *B01L 3/50273* (2013.01); *B01L 3/502753* (2013.01); *B01L 3/502761* (2013.01); *G01N 21/05* (2013.01); *G01N 33/54366* (2013.01); *B01F 2005/0636* (2013.01); *B01L 2200/0668* (2013.01); *B01L 2300/0867* (2013.01); *B01L 2300/0877* (2013.01); *B01L 2300/123* (2013.01); *B01L 2400/043* (2013.01); *B01L 2400/0415* (2013.01); *B01L 2400/0433* (2013.01); *B01L 2400/0442* (2013.01); *B01L 2400/0454* (2013.01); *B01L 2400/086* (2013.01)

(58) Field of Classification Search
CPC ...... B01F 5/061; B01F 5/0609; B01F 5/0602; B01F 5/06; B01L 3/50273; B01L 3/5027; B01L 3/507; B01L 3/50; B01L 3/00
USPC .......................................... 422/502, 500, 50
See application file for complete search history.

(56) References Cited

U.S. PATENT DOCUMENTS 8,586,368 B2 * 11/2013 Superfine ........... G01N 33/4905
436/69
2013/0074613 A1 * 3/2013 Jeon .................. B01L 3/502753
73/864

* cited by examiner

FLOW CELLS UTILIZING SURFACE-ATTACHED STRUCTURES, AND RELATED SYSTEMS AND METHODS

CROSS-REFERENCE TO RELATED APPLICATIONS

The present application is a 371 national phase entry of international application PCT/US2016/052463, filed Sep. 19, 2016, which claims priority to provisional patent application No. 62/347,046 filed Jul. 7, 2016 and to provisional patent application No. 62/220,906 filed Sep. 18, 2015, which are incorporated herein by reference in their entireties.

TECHNICAL FIELD

This present invention generally relates to flow cells and systems and methods utilizing flow cells for processing fluids containing analytes or other targets of interest. In particular, the invention relates to flow cells that utilize surface-attached structures, and related systems and methods.

BACKGROUND

A wide variety of techniques involve the isolation or extraction of one or more selected components from a fluid for analytical or purification purposes, such as immunoassays, centrifugation, filtering, chromatography, solid phase extraction (SPE), and others. Conventional techniques include the use of steric filters and columns of packed beads, both of which are prone to clogging. Magnetic beads have also been utilized, but generally cannot achieve the superior surface area-to-volume ratio offered by packed columns unless a very large number of magnetic beads are utilized. To reduce clogging, pre-separation techniques may be utilized such as pre-filters, guard columns, centrifugation, pipetting, etc., but such measures add to the complexity, cost, and size of the associated system.

In addition, there are currently many assays in which a fluid sample is placed into a microfluidic chamber and then made to wash over capture sites on a microarray (e.g., dots of reagents, oligonucleotides, proteins, etc.). In such assays, the fluid sample sits for a period of time to allow for the reaction of analytes in the fluid sample with the capture sites on the microarray. Typically, such assays allow the analytes in the fluid sample to flow throughout the chamber by diffusion, resulting in very long reaction times that can last for multiple days. For devices in which short reaction times are important (e.g., point of care (POC) devices), the reaction has to be stopped before all of the analyte has had time to diffuse to corresponding capture sites, resulting in low analyte utilization and analyte waste.

Therefore, there is a need for devices, systems, and methods for isolating or extracting one or more selected components from a fluid that minimize or avoid clogging. There is also a need for a device capable of isolating or extracting one or more selected components from a fluid flowing through the device, and which is inherently structured to minimize clogging and/or provides a structure may be actively operated to prevent or disrupt clogging. Furthermore, there is a need for devices, systems, and methods for enhancing flow, circulation, and/or mixing action for analyte capture on a microarray.

SUMMARY

To address the foregoing problems, in whole or in part, and/or other problems that may have been observed by persons skilled in the art, the present disclosure provides methods, processes, systems, apparatus, instruments, and/or devices, as described by way of example in implementations set forth below.

According to one embodiment, a flow cell includes: a chamber enclosing an interior and comprising a fluid inlet, a fluid outlet, and an inside surface facing the interior; and a plurality of surface-attached structures attached to the inside surface at a plurality of respective attachment sites and extending into the interior therefrom, each surface-attached structure comprising a flexible body and a metallic component disposed on or in the body, wherein application of a magnetic or electric field actuates the surface-attached structure into movement relative to the corresponding attachment site.

According to another embodiment, a flow cell includes: a plurality of flow cell units, each flow cell unit comprising a chamber and a plurality of surface-attached structures according to any of the embodiments disclosed herein, wherein the plurality of flow cell units has a configuration selected from the group consisting of: the flow cell units are stacked in parallel; and the flow cell units are arranged in series such that the fluid inlet or the fluid outlet of each flow cell unit communicates with the fluid inlet or the fluid outlet of at least one other flow cell unit.

According to an embodiment, a flow cell includes: a chamber enclosing an interior and comprising a fluid inlet, a fluid outlet, and an inside surface facing the interior; and a plurality of surface-attached structures attached to the inside surface at a plurality of respective attachment sites and extending into the interior therefrom, each surface-attached structure comprising a flexible body and a metallic component disposed on or in the body, wherein application of a magnetic or electric field actuates the surface-attached structure into movement relative to the corresponding attachment site.

According to another embodiment, a flow cell includes: a chamber enclosing an interior and comprising a fluid inlet, a fluid outlet, and an inside surface facing the interior; and a plurality of surface-attached structures attached to the inside surface at a plurality of respective attachment sites and extending into the interior therefrom, each surface-attached structure being movable in response to an actuation force selected from the group consisting of: a magnetic force, a thermal force, a sonic force, an optical force, an electrical force, and a vibrational force.

According to another embodiment, the flow cell includes a binding agent configured for binding to a target present in the interior. The binding agent may be disposed on or integrated with an outer surface of at least some of the surface-attached structures, or disposed on or integrated with the inside surface, or both of the foregoing.

According to another embodiment, the flow cell includes a plurality of binding agents, wherein at least some of the binding agents are arranged as a microarray spaced from the plurality of surface-attached structures by a gap in the interior.

According to another embodiment, a target extraction system includes: a flow cell according to any of the embodiments disclosed herein; a driver configured for applying a magnetic force, and electric force, or other actuation force to the interior of the flow cell to actuate movement of the surface-attached structures. In some embodiments, the target extraction system includes a housing configured for removably receiving the flow cell.

According to another embodiment, a method for extracting a target from a sample includes: flowing a target-containing sample through a flow cell and into contact with surface-attached structures disposed in the flow cell, wherein the surface-attached structures are attached to an inside surface of the flow cell at a plurality of respective attachment sites, and the surface-attached structures are movable in the flow cell relative to the attachment sites in response to magnetic or electric actuation; and while flowing the sample, isolating targets of the sample from a remaining portion of the sample.

According to another embodiment, a method for extracting a target from a sample includes: flowing a target-containing sample through a flow cell and into contact with surface-attached structures disposed in the flow cell, wherein the surface-attached structures are attached to an inside surface of the flow cell at a plurality of respective attachment sites, and the surface-attached structures are movable in the interior relative to the attachment sites in response to magnetic or electric actuation; and while flowing the sample, capturing the targets on the surface-attached structures, or on the inside surface, or on both the surface-attached structures and the inside surface, and wherein capturing produces a depleted sample containing a reduced concentration of the targets.

According to another embodiment, a method for extracting a target from a sample includes: flowing a target-containing sample through a flow cell and into contact with surface-attached structures disposed in the flow cell, wherein the surface-attached structures are attached to an inside surface of the flow cell at a plurality of respective attachment sites, and the surface-attached structures are movable in the flow cell relative to the attachment sites in response to magnetic or electric actuation; and while flowing the sample, applying a magnetic or electric field to the flow cell to actuate movement of the surface-attached structures.

According to another embodiment, a flow cell or system is configured for performing any of the methods disclosed herein.

Other devices, apparatus, systems, methods, features and advantages of the invention will be or will become apparent to one with skill in the art upon examination of the following figures and detailed description. It is intended that all such additional systems, methods, features and advantages be included within this description, be within the scope of the invention, and be protected by the accompanying claims.

BRIEF DESCRIPTION OF THE DRAWINGS

The invention can be better understood by referring to the following figures. The components in the figures are not necessarily to scale, emphasis instead being placed upon illustrating the principles of the invention. In the figures, like reference numerals designate corresponding parts throughout the different views.

DETAILED DESCRIPTION

Definitions

Figure 1A:
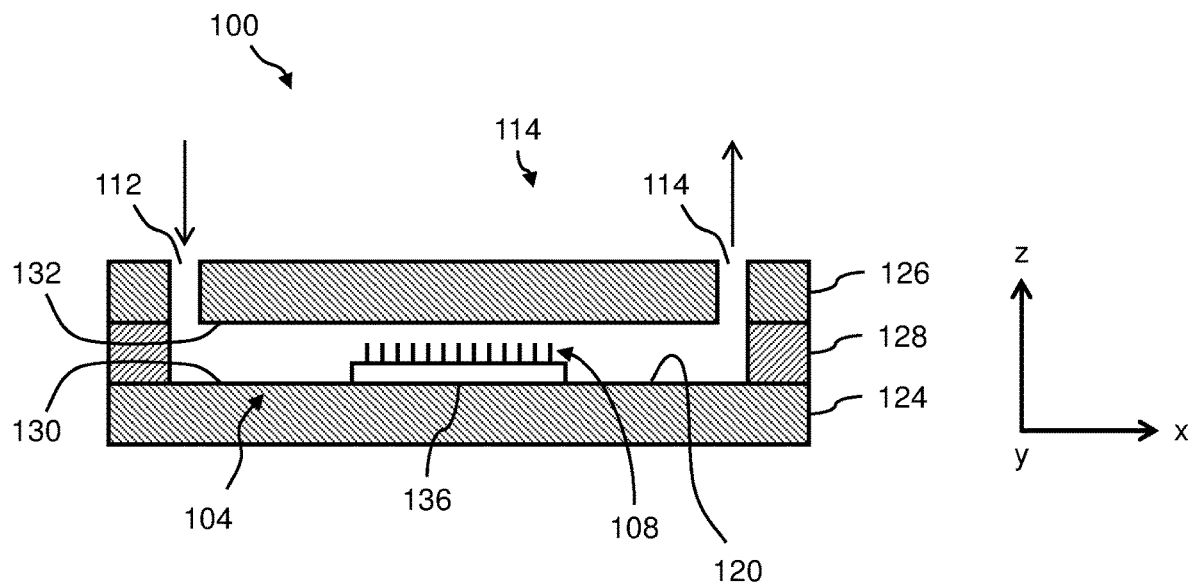
FIG. 1A is a schematic cross-sectional elevation view of an example of a flow cell according to some embodiments.

Unless defined otherwise, all technical and scientific terms used herein have the meaning commonly understood by a person skilled in the art to which this invention belongs.

Following long-standing patent law convention, the terms "a," "an," and "the" refer to "one or more" when used in this application, including the claims. Thus, for example, reference to "a subject" includes a plurality of subjects, unless the context clearly is to the contrary (e.g., a plurality of subjects), and so forth.

Throughout this specification and the claims, the terms "comprise," "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some embodiments, ±100% in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the term "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range (for example, the recitation of 1 to 5 includes 1, 2, 3, 4, and 5, as well as fractions thereof, e.g., 1.5, 2.25, 3.75, 4.1, and the like) and any range within that range.

As used herein, a "target" is any particle (or bioparticle) carried in a fluid (typically a liquid) such as by entrainment, suspension or colloidal dispersion, for which isolation from the fluid is desired. Examples of targets include, but are not limited to, a biological cell; an intracellular component; a microbe; a pathogen such as a bacterium, a virus, a prion, or a fungus; a carcinogen; an antigen; a hapten; an antibody (e.g., immunoglobulin); an animal or anti-human antibody (e.g., antiglobulin); a toxin; a drug; a steroid; a vitamin; a biopolymer such as a protein, a carbohydrate, or a nucleic acid; a biological compound such as a peptide; a hormone; an allergen; pesticide; a chemical compound; a molecule; a chemical element (e.g., a trace metal); a fragment, particle, or partial structure of any of the foregoing; and binding partners of any of the foregoing. In some cases the target may be a rare particle in the fluid, and isolation of the rare particle is desired in order to concentrate the rare particle for subsequent analysis thereof, or to purify the fluid by removing the rare particle therefrom, etc.

In some embodiments, the target is an analyte—that is, it is desired to isolate the target for the purpose of measuring a property or attribute thereof, or for detecting its presence in the fluid. In other embodiments, the target is a non-analyte. For example, the non-analyte target may be isolated from a fluid for the purpose of purging the fluid of the target, or for analyzing the fluid (or components thereof) in the absence of the target. As another example, the non-analyte target may be considered as an interferent or suppressant, or as contributing only to background signal, such that it is desired to analyze the fluid without the target being present, or to subject the fluid to a reaction without the target being present. In these latter cases the fluid, or a species of the fluid other than the target to be isolated, may be an analyte of interest.

As used herein, the term "fluid sample" generally refers to any flowable substance, i.e., a substance that can flow passively or actively (e.g., by pumping) through a fluid conduit such as a tube, channel, or chamber. The fluid sample may be, for example, a bodily (human or animal) fluid (e.g., blood, serum, plasma, other fluids), a solution containing a biological tissue or cell, a solution derived from the environment (e.g., surface water, or a solution containing plant or soil components), a solution derived from food, or a solution derived from a chemical or pharmaceutical process (e.g., reaction, synthesis, dissolution, etc.). A fluid sample may be known to contain or suspected of containing one or more targets, which may be isolated or extracted from the fluid sample in accordance with methods disclosed herein.

As used herein, the term "binding agent" or "binding partner" refers to any molecule capable of binding to another molecule, i.e., to another binding partner such as a "target" as described herein. Thus, examples of binding agents include, but are not limited to, a biological cell; an intracellular component; a microbe; a pathogen such as a bacterium, a virus, a prion, or a fungus; a carcinogen; an antigen; a hapten; an antibody (e.g., immunoglobulin); an animal or anti-human antibody (e.g., antiglobulin); a toxin; a drug; a steroid; a vitamin; a biopolymer such as a protein, a carbohydrate, or a nucleic acid; a biological compound such as a peptide; a hormone; an allergen; a pesticide; a chemical compound; a molecule; a chemical element (e.g., a trace metal); a fragment, particle, or partial structure of any of the foregoing; and binding partners of any of the foregoing. Examples of molecules that are binding partners to each other include, but are not limited to, antibody-antigen, antibody-hapten, hormone-hormone receptor, lectin-carbohydrate, enzyme-enzyme inhibitor (or enzyme cofactor), biotin-avidin (or streptavidin) (including derivatives of biotin and avidin), ligand-ligand receptor, protein-immunoglobulin, and nucleic acid-complementary nucleic acid (e.g., complementary oligonucleotides, DNA or RNA). Depending on the type of assay being implemented, a binding partner may be an analyte to be detected, or may be an intermediate binding partner utilized in various ways in the course of detecting the analyte.

In some embodiments, a binding agent is capable of being surface-immobilized by a suitable technique such as, for example, surface functionalization, coating, etc., whereby the binding agent is consequently disposed on or integrated with a surface. Examples of surface functionalization techniques include, but are not limited to, physisorption, graft polymerization, electrostatic interaction, covalent coupling, and biotin-(strept)avidin coupling. Depending on the type of binding agent utilized, the binding agent may be bound or attached to the surface with or without the need for an intermediary binder or linker or cross-linker molecule. Depending on the type of binding agent utilized, the surface to be functionalized or coated may need to be prepared or pre-treated (e.g., silanization, solvent extraction, solvent impregnation), as appreciated by persons skilled in the art. A surface-immobilized binding agent may also be referred to as a "receptor" in some embodiments.

In some embodiments, a binding agent may be a "binding-specific" agent. As used herein, a binding-specific agent is one that has a high affinity for and readily binds to a specific type of binding partner, and which under normal assaying conditions does not bind to any other type of molecule. As an example, a binding-specific agent may be an antibody that will only bind to a specific type of antigen, antigen analog or hapten. Depending on the assay format implemented, a binding-specific agent may be an analyte-specific receptor, i.e., may act as a direct binding partner for the analyte to be detected in a fluid sample or for a conjugate of the analyte or a complex containing the analyte. Alternatively, a binding-specific agent may be a binding partner for another non-analyte binding partner, and that other non-analyte binding partner may in turn be a specific binding partner for the analyte to be detected.

The occurrence of a binding-specific agent binding to a specific type of binding partner may be referred to as a "specific binding" event. On the other hand, a "non-specific binding" event or "non-specific adsorption" (NSA) event as used herein generally refers to the occurrence of a component of a fluid sample (e.g., a non-target or non-analyte) binding to a surface by a mechanism other than the specific recognition that characterizes a specific binding event.

As used herein, the term "(bio)chemical compound" encompasses chemical compounds and biological compounds. A chemical compound may, for example, be a small molecule or a high molecular-weight molecule (e.g., a polymer). A biological compound may be, for example, a biopolymer.

As used herein, the term "oligonucleotide" denotes a biopolymer of nucleotides that may be, for example, 10 to 300 or greater nucleotides in length. Oligonucleotides may be synthetic or may be made enzymatically. Oligonucleotides may contain ribonucleotide monomers (i.e., may be oligoribonucleotides) and/or deoxyribonucleotide monomers (i.e., may be oligodeoxyribonucleotides). Oligonucleotides may include modified nucleobases. Oligonucleotides may be synthesized as part of or in preparation for methods disclosed herein, or may be pre-synthesized and provided as a starting material for methods disclosed herein. For convenience, oligonucleotides are also referred to herein by the short-hand term "oligos." Oligos utilized to assemble synthons may be referred to herein as "synthon precursor oligos" to distinguish them from other types of oligos that may be utilized or present in the methods and systems, such as the probes of a capture array and adaptor oligos (AOs).

The terms "nucleic acid" and "polynucleotide" are used interchangeably herein to describe a polymer of any length, e.g., greater than about 2 bases, greater than about 10 bases, greater than about 100 bases, greater than about 500 bases, greater than 1000 bases, up to about 10,000 or more bases composed of nucleotides, e.g., deoxyribonucleotides or ribonucleotides, and may be produced enzymatically or synthetically (e.g., PNA as described in U.S. Pat. No. 5,948,902 and the references cited therein) and which can hybridize with naturally occurring nucleic acids in a sequence specific manner analogous to that of two naturally occurring nucleic acids, e.g., can participate in Watson-Crick base pairing interactions. In addition to deoxyribonucleic acid (DNA) and ribonucleic acid (RNA), the terms "nucleic acid" and "polynucleotide" may encompass peptide nucleic acid (PNA), locked nucleic acid (LNA), and unstructured nucleic acid (UNA). Nucleic acids or polynucleotides may be synthesized using methods and systems disclosed herein.

As used herein, the term "releasing" in the context of releasing an oligo from the surface of a support structure refers to breaking or overcoming a bond or cleavage site of the oligo such that all or part of the oligo is freed (or unbound, liberated, detached, untethered, de-anchored, etc.) from the surface. Typically, releasing an oligo entails "cleaving" the oligo such as by chemical cleaving, enzymatic cleaving, and photocleaving techniques, as appropriate for the particular embodiment.

Certain embodiments disclosed herein entail the use of "surface-attached structures." Generally, a surface-attached structure has two opposing ends: a fixed end and a free end. The fixed end may be attached to a substrate by any suitable means, depending on the fabrication technique and materials employed. The fixed end may be "attached" by being integrally formed with or adjoined to the substrate, such as by a microfabrication process. Alternatively, the fixed end may be "attached" via a bonding, adhesion, fusion, or welding process. The surface-attached structure has a length defined from the fixed end to the free end, and a cross-section lying in a plane orthogonal to the length. For example, using the Cartesian coordinate system as a frame of reference, and associating the length of the surface-attached structure with the z-axis (which may be a curved axis), the cross-section of the surface-attached structure lies in the x-y plane. Generally, the cross-section of the surface-attached structure may have any shape, such as rounded (e.g., circular, elliptical, etc.), polygonal (or prismatic, rectilinear, etc.), polygonal with rounded features (e.g., rectilinear with rounded corners), or irregular. The size of the cross-section of the surface-attached structure in the x-y plane may be defined by the "characteristic dimension" of the cross-section, which is shape-dependent. As examples, the characteristic dimension may be diameter in the case of a circular cross-section, major axis in the case of an elliptical cross-section, or maximum length or width in the case of a polygonal cross-section. The characteristic dimension of an irregularly shaped cross-section may be taken to be the dimension characteristic of a regularly shaped cross-section that the irregularly shaped cross-section most closely approximates (e.g., diameter of a circle, major axis of an ellipse, length or width of a polygon, etc.).

A surface-attached structure as disclosed herein is movable (flexible, deflectable, bendable, etc.) relative to its fixed end or point of attachment to the substrate. To facilitate its movability, the surface-attached structure may include a flexible body composed of an elastomeric (flexible) material, and may have an elongated geometry in the sense that the dominant dimension of the surface-attached structure is its length—that is, the length is substantially greater than the characteristic dimension. Examples of the composition of the flexible body include, but are not limited to, elastomeric materials such as polydimethylsiloxane (PDMS).

The overall shape or geometry of the surface-attached structure may be generally cylindrical, polygonal, or a combination of cylindrical and polygonal features. Examples include, but are not limited to, posts, pillars, rods, bars, paddles, blades, and the like having circular/elliptical or rectilinear cross-sections. The characteristic dimension of the surface-attached structure may be generally constant along its length, or may vary gradually or in a stepped manner. For example, the surface-attached structure may be conical or pyramidal, with the characteristic dimension tapering down in the direction either toward the free end or toward the fixed end. As another example, a selected portion of the surface-attached structure may have a smaller characteristic dimension than that of the remaining portion of the surface-attached structure. This may be done, for example, to enhance flexure of the surface-attached structure at that selected portion.

In some embodiments, the surface-attached structure has at least one dimension (length or characteristic dimension) on the order of micrometers (e.g., from about 1 µm to about 1000 µm) or nanometers (e.g., less than about 1 µm (1000 nm)). In such micro-scale embodiments, the surface-attached structures may be fabricated in accordance with techniques practiced in or derived from various fields of microfabrication such as microfluidics, microelectronics, microelectromechanical systems (MEMS), and the like, now known or later developed.

The surface-attached structure is configured such that the movement of the surface-attached structure relative to its fixed end may be actuated or induced in a non-contacting manner, specifically by an applied magnetic or electric field of a desired strength, field line orientation, and frequency (which may be zero in the case of a magnetostatic or electrostatic field). To render the surface-attached structure movable by an applied magnetic or electric field, the surface-attached structure may include an appropriate metallic component disposed on or in the flexible body of the surface-attached structure. To render the surface-attached structure responsive to a magnetic field, the metallic component may be a ferromagnetic material such as, for example, iron, nickel, cobalt, or magnetic alloys thereof, one non-limiting example being "alnico" (an iron alloy containing aluminum, nickel, and cobalt). To render the surface-attached structure responsive to an electric field, the metallic component may be a metal exhibiting good electrical conductivity such as, for example, copper, aluminum, gold, and silver, and well as various other metals and metal alloys. Depending on the fabrication technique utilized, the metallic component may be formed as a layer (or coating, film, etc.) on the outside surface of the flexible body at a selected region of the flexible body along its length. The layer may be a continuous layer or a densely grouped arrangement of particles. Alternatively, the metallic component may be formed as an arrangement of particles embedded in the flexible body at a selected region thereof.

In other embodiments, the actuation force may be a thermal force, a sonic force, an optical force, or a vibrational force.

A microfluidic device or system as disclosed herein may be composed of a material, for example, of the type utilized in various fields of microfabrication such as microfluidics, microelectronics, micro-electromechanical systems (MEMS), and the like. The composition of the material may be one that is utilized in these fields as a semiconductor, electrical insulator or dielectric, vacuum seal, structural layer, or sacrificial layer. The material may thus be composed of, for example, a metalloid (e.g., silicon or germanium), a metalloid alloy (e.g., silicon-germanium), a carbide such as silicon carbide, an inorganic oxide or ceramic (e.g., silicon oxide, titanium oxide, or aluminum oxide), an inorganic nitride or oxynitride (e.g., silicon nitride or silicon oxynitride), various glasses, or various polymers such as polycarbonates (PC), polydimethylsiloxane (PDMS), etc. A solid body of the material may initially be provided in the form of, for example, a substrate, a layer disposed on an underlying substrate, a microfluidic chip, a die singulated from a larger wafer of the material, etc.

A microfluidic conduit (e.g., channel, chamber, port, etc.) may be formed in a solid body of material by any technique, now known or later developed in a field of fabrication, which is suitable for the material's composition and the size and aspect ratio (e.g., length:diameter) of the channel. As non-limiting examples, the conduit may be formed by an etching technique such as focused ion beam (FIB) etching, deep reactive ion etching (DRIE), soft lithography, or a micromachining technique such as mechanical drilling, laser drilling or ultrasonic milling. Depending on the length and characteristic dimension of the conduit to be formed, the etching or micromachining may be done in a manner analogous to forming a vertical or three-dimensional "via" partially into or entirely through the thickness of the material (e.g., a "through-wafer" or "through-substrate" via). Alternatively, an initially open conduit or trench may be formed on the surface of a substrate, which is then bonded to another substrate to complete the conduit. The other substrate may present a flat surface, or may also include an initially open conduit that is aligned with the open conduit of the first substrate as part of the bonding process.

Depending on its composition, the material defining the conduit may be inherently chemically inert relative to the fluid flowing through the conduit. Alternatively, the conduit (or at least the inside surface of the conduit) may be deactivated as part of the fabrication process, such as by applying a suitable coating or surface treatment/functionalization so as to render the conduit chemically inert and/or of low absorptivity to the material. Moreover, the inside surface of the conduit may be treated or functionalized so as to impart or enhance a property such as, for example, hydrophobicity, hydrophilicity, lipophobicity, lipophilicity, low absorptivity, etc., as needed or desirable for a particular application. Alternatively or additionally, the outside of the conduit may also be treated or functionalized similarly. Coatings and surface treatments/functionalizations for all such purposes are readily appreciated by persons skilled in the art.

In some embodiments, the material forming the conduit is optically transparent for a purpose such as performing an optics-based measurement, performing a sample analysis, detecting or identifying a substance flowing through the conduit, enabling a user to observe flows and/or internal components, etc.

It will be understood that terms such as "communicate" and "in communication with" (for example, a first component "communicates with" or "is in communication with" a second component) are used herein to indicate a structural, functional, mechanical, electrical, signal, optical, magnetic, electromagnetic, ionic or fluidic relationship between two or more components or elements. As such, the fact that one component is said to communicate with a second component is not intended to exclude the possibility that additional components may be present between, and/or operatively associated or engaged with, the first and second components.

Flow Cells Utilizing Surface-Attached Structures and Related Systems and Methods FIG. 1A is a schematic cross-sectional elevation view of an example of a flow cell 100 according to some embodiments. Specifically, FIG. 1A is a view of the flow cell 100 along its length. For descriptive purposes, FIG. 1A and other figures include a Cartesian coordinate frame of reference, which has been arbitrarily oriented such that the length of the flow cell 100 is in the direction of the x-axis, the width of the flow cell 100 is in the direction of the y-axis (through the drawing sheet), and the height of the flow cell 100 is in the direction of the z-axis.

Generally, the flow cell 100 includes a chamber 104 enclosing a chamber interior and a plurality of surface-attached structures 108. The chamber 104 includes a fluid inlet 112 and a fluid outlet 114 communicating with the chamber interior, and an inside surface 120 (i.e., one or more inside surfaces) facing the chamber interior and serving as boundaries thereof. The inside surface 120 may define all or most of the volume of the chamber interior. In some embodiments, the interior volume may be on the order of microliters (e.g., less than about 1000 µL). In some embodiments, the overall dimensions of the flow cell 100 (length, width, height) may be on the order of millimeters (e.g., from about 1 mm to about 1000 mm) or micrometers. The flow cell 100 may be coupled to a fluidic circuit by any suitable means, such as by utilizing appropriate fittings coupled to the fluid inlet 112 and the fluid outlet 114 as appreciated by persons skilled in the art. The flow cell 100 may establish a flow of fluid (typically liquid) from the fluid inlet 112, through the chamber 104, and to the fluid outlet 114, as indicated by arrows in FIG. 1A.

Generally, no limitation is placed on the structural configuration of the chamber 104 or on the manner in which the chamber 104 is fabricated. In the embodiment illustrated in FIG. 1A, the chamber 104 includes a first layer 124 (or base), a second layer 126 (or cover or lid), and a third layer 128 (or intermediate layer, or spacer) between the first layer 124 and the second layer 126. From the perspective of FIG. 1A, the first layer 124 may be considered as a bottom layer and the second layer 126 may be considered as a top layer, in the sense that the first layer 124 is above the second layer 126 and the first layer 124 and second layer 126 are both above an underlying surface that supports the flow cell 100 (e.g., benchtop, floor, ground, etc.). The first layer 124 includes a first inside surface 130 facing the chamber interior, and the second layer 126 includes a second inside surface 132 facing the chamber interior opposite to the first inside surface 130. The first layer 124 (and first inside surface 130) is spaced from the second layer 126 (and second inside surface 132) by the third layer 128, which in the present embodiment defines the height of the chamber 104. Also in the present embodiment, inside surfaces of the third layer 128 define the shape of the chamber 104 in the plane orthogonal to the drawing sheet of FIG. 1A. The third layer 128 and the configuration of the chamber 104 are best shown in FIG. 1B, which is a cross-sectional top plan view of the flow cell 100 with the second layer 126 removed, and thus is a view of the flow cell 100 along its width.

In the illustrated embodiment, the fluid inlet 112 and the fluid outlet 114 have been arbitrarily located on the same side of the flow cell 100, specifically the top side. In this case, the fluid inlet 112 and the fluid outlet 114 are defined in part by bores (vias) formed (such as by laser drilling) through the second layer 126 that are aligned with corresponding openings in the third layer 128. Positioning the fluid inlet 112 and the fluid outlet 114 on the same side may facilitate certain fabrication techniques. More generally, however, the fluid inlet 112 and the fluid outlet 114 may be located on different sides of the flow cell 100 (e.g., top and bottom, opposing ends, etc.).

The surface-attached structures 108 may be configured generally as described above. The plurality of surface-attached structures 108 is attached to the inside surface 120 of the chamber 104 at a plurality of respective attachment sites, such that the surface-attached structures 108 extend into the chamber interior from the inside surface 120. In the illustrated embodiment, the surface-attached structures 108 are attached to a substrate 136 distinct from the first layer 124 of the flow cell 100, and the substrate 136 is attached to the first layer 124. It may be advantageous to form the surface-attached structures 108 on a distinct substrate 136 in one process, and then attach the surface-attached structures 108 to the inside surface 120 (by way of the intervening substrate 136) in a separate process. After being attached to the inside surface 120, the substrate 136 faces the chamber interior and serves as a boundary of the chamber interior, and thus the substrate 136 may be considered as being part of the inside surface 120. Hence, the description of the surface-attached structures 108 being "attached to the inside surface" encompasses embodiments in which a distinct substrate 136 supporting the surface-attached structures 108 is utilized. Alternatively, the surface-attached structures 108 may be directly attached to a layer of the chamber 104 such as the first layer 124.

Figure 1B:
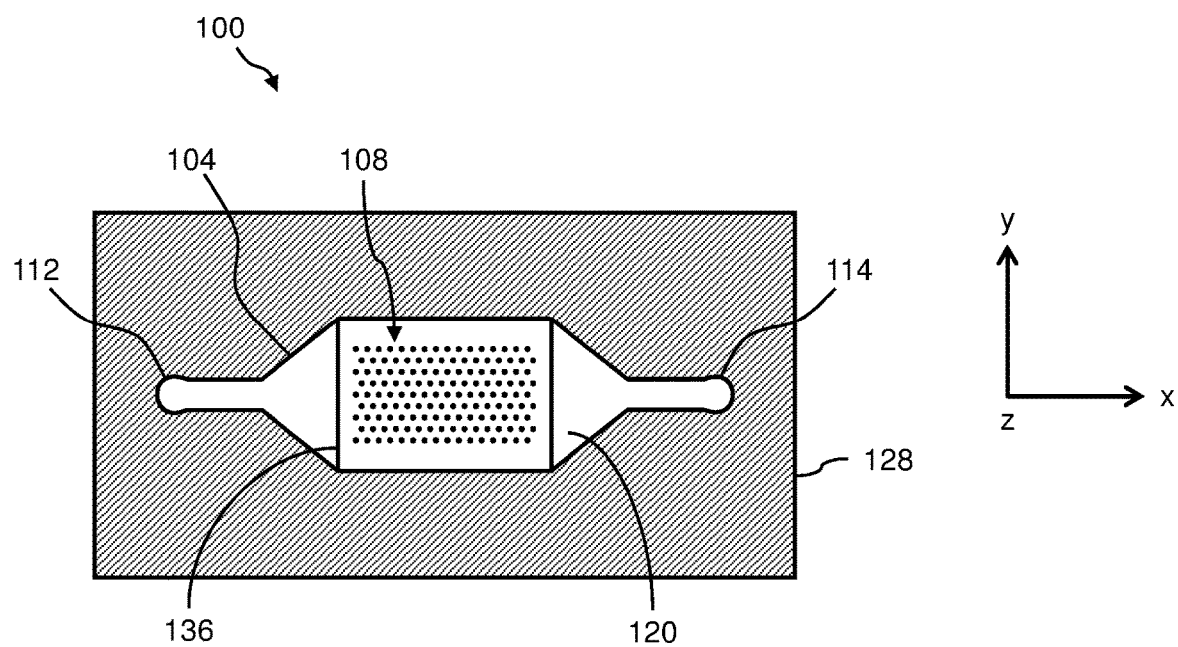
FIG. 1B is a cross-sectional top plan view of the flow cell illustrated in FIG. 1A with a top layer thereof removed.

Referring to FIG. 1B, the surface-attached structures 108 may be arranged in a two-dimensional array. Neighboring (adjacent) surface-attached structures 108 are spaced from each other by an "inter-structure spacing," i.e., the distance between two neighboring surface-attached structures 108. The array may be ordered in a substantially uniform manner, in which case the inter-structure spacing is substantially constant throughout the array. Alternatively, the array may be somewhat randomly ordered, in which case the inter-structure spacing may vary within some range of distance values. In some embodiments, the plurality of surface-attached structures 108 has an inter-structure spacing on the order of micrometers or nanometers. In the case of a randomly ordered array of surface-attached structures 108, the inter-structure spacing may be taken to be the average inter-structure spacing of the array. In some embodiments, the inter-structure spacing may be effective for performing separation by size exclusion or filtration on a target-containing sample flowing through the chamber 104.

As also shown in FIG. 1B, the surface-attached structures 108 may be positioned in the fluid flow path established by the flow cell 100, e.g., in the chamber 104 between the fluid inlet 112 and the fluid outlet 114. Hence, a fluid flowing through the flow cell 100 will come into contact with the surface-attached structures 108. This configuration enables the surface-attached structures 108 to interact with the fluid, or with one or more desired components of the fluid, as described further below. The size and density (inter-structure spacing) of the surface-attached structures 108 may be selected to increase the probability of contact or interaction with a desired component of the fluid. In some embodiments, the number and size of the surface-attached structures 108 and their inter-structure spacing may be such as to increase the surface area in the chamber 104 by about two times (2×) or greater, or in another example from about two times (2×) to about six times (6×) greater, as compared to the chamber 104 without the surface-attached structures 108. In some embodiments, the number density of the surface-attached structures 108 may be in a range from $10^3$ to $10^6$ structures/cm$^2$. Moreover, as shown in FIG. 1B the array of surface-attached structures 108 may span substantially the entire width (in the vertical direction from the perspective of FIG. 1B) of the chamber 104 to increase the probability of contact or interaction.

As described elsewhere in the present disclosure, the surface-attached structures 108 are movable by an applied magnetic or electric field. Because the structures 108 are attached to an underlying surface, they do not aggregate in the presence of the magnetic or electric field, unlike magnetic beads which do aggregate in response to a magnetic field.

Figure 2A:
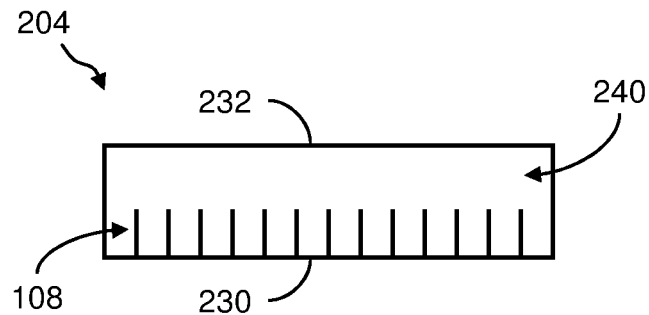
FIG. 2A is a schematic elevation view of an example of a chamber of a flow cell according to one embodiment.
Figure 2B:
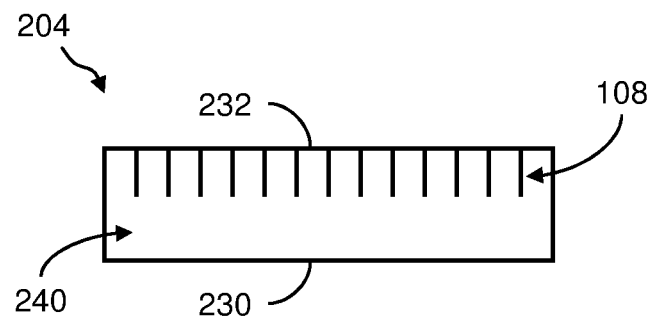
FIG. 2B is a schematic elevation view of an example of a chamber of a flow cell according to another embodiment.
Figure 2C:
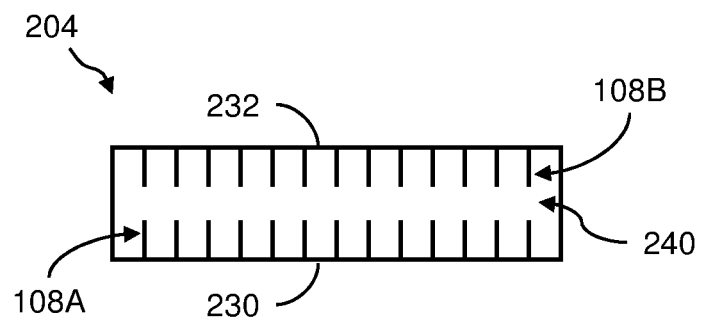
FIG. 2C is a schematic elevation view of an example of a chamber of a flow cell according to another embodiment.

As described above, the plurality of surface-attached structures 108 is attached to the inside surface 120 of the chamber 104 at a plurality of respective attachment sites. Generally, the surface-attached structures 108 may be attached to any part of the inside surface 120, and some surface-attached structures 108 may be attached to one part while other surface-attached structures 108 are attached to a different part. FIGS. 2A, 2B, and 2C illustrate a few examples of possible arrangements of the surface-attached structures 108.

Specifically, FIG. 2A is a schematic elevation view of an example of a chamber 204 (along either its length or width) of a flow cell according to one embodiment. The inside surface of the chamber 204 includes a first (or bottom) inside surface 230 and an opposing second (or top) inside surface 232, both facing the chamber interior and spaced from each other such that chamber interior is between them. The flow cell (specifically, the chamber 204 in the present embodiment) includes an array of surface-attached structures 108 as described above. In the embodiment of FIG. 2A (similar to that of FIGS. 1A and 1B), the surface-attached structures 108 are attached to the first inside surface 230 at a plurality of respective attachment sites, and thus extend generally upward and into the chamber interior from the first inside surface 230. As also shown in FIG. 2A, the length of the surface-attached structures 108 (or height in the current perspective) is less than the height of the chamber interior (between the first inside surface 230 and the second inside surface 232). Consequently, the chamber interior includes a structure-free region or gap 240 (i.e., a three-dimensional space devoid of surface-attached structures 108) between the surface-attached structures 108 and the second inside surface 232.

Generally, the intended effects of the region containing the surface-attached structures 108 and the structure-free region 240, respectively, on the fluid (and/or components thereof) flowing through the chamber 204 from the fluid inlet to the fluid outlet may vary depending on the application. Moreover, the relative lengths (or heights) of the surface-attached structures 108 and the structure-free region 240 may vary depending on the application. For example, in some embodiments the length of the structure-free region 240 may be less than the length of the surface-attached structures 108, whereby a majority of the flowing fluid encounters the structure-free region 240. In other embodiments, the length of the structure-free region 240 may be greater than or about equal to the length of the surface-attached structures 108. In some embodiments, the length of the structure-free region 240 may be minimized to increase the probability of contact or interaction with a desired component of the fluid, as the fluid may otherwise preferentially flow through the structure-free region 240 where flow resistance is lower. As one non-limiting example, the length of the structure-free region 240 may be about 10 μm, while in other examples may be more or less than 10 μm.

FIG. 2B is a schematic elevation view of the chamber 204 according to another embodiment. In this embodiment, the surface-attached structures 108 are attached to the second inside surface 232 at a plurality of respective attachment sites, and thus extend generally downward and into the chamber interior from the second inside surface 232. The structure-free region 240 is thus below instead of above the surface-attached structures 108.

FIG. 2C is a schematic elevation view of the chamber 204 according to another embodiment. In this embodiment, the flow cell includes an array of first surface-attached structures 108A attached to the first inside surface 230 at a plurality of respective attachment sites, and an array of second surface-attached structures 108B attached to the second inside surface 232 at a plurality of respective attachment sites. Consequently, the structure-free region 240 is located between the first inside surface 230 and the second inside surface 232.

Generally, the positioning of the surface-attached structures 108 in the chamber 204 may depend upon the application. For example, in a given application, gravitational and/or density-related effects on one or more components of the fluid may dictate whether to position surface-attached structures 108 on the first inside surface 230 (FIG. 2A), on the second inside surface 232 (FIG. 2B), or on both inside surfaces 230 and 232 (FIG. 2C). As another example, the structure-free region 240 when positioned below the surface-attached structures 108 (FIG. 2B) may serve as a collection region for sediments or precipitates. As another example, providing two or more sets of surface-attached structures 108 having different configurations may be desirable in a given application. For example, in the embodiment shown in FIG. 2C, the first surface-attached structures 108A may be configured differently than the second surface-attached structures 108B. As an example of different configurations, the first surface-attached structures 108A may have an inter-structure spacing different from that of the second surface-attached structures 108B, such as to achieve two different size exclusion or filtering effects on the fluid flowing through the chamber 204. As another example of different configurations, the first surface-attached structures 108A may include a binding agent (described below) while the second surface-attached structures 108B do not (or vice versa). Alternatively, the first surface-attached structures 108A may include a binding agent specific for capturing one type of target in a fluid sample, while the second surface-attached structures 108B include a binding agent specific for capturing a different type of target in the same fluid sample.

In embodiments described thus far, the surface-attached structures 108 are located on the top or bottom inside surface of a chamber. Additionally or alternatively, however, surface-attached structures 108 may be located on a laterally oriented (side-oriented) inside surface of the chamber, such that the surface-attached structures 108 extend in a direction generally parallel with the top or bottom inside surface of the chamber.

Figure 3A:
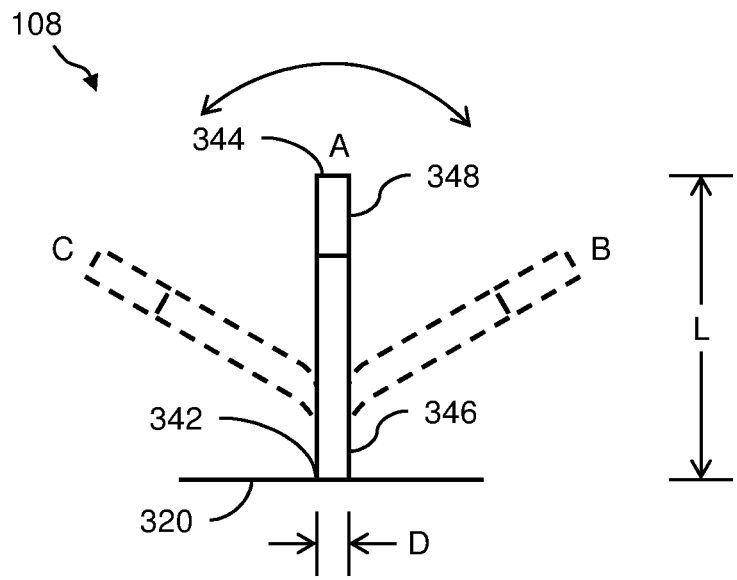
FIG. 3A is a schematic elevation view of an example of a single surface-attached structure according to some embodiments.

FIG. 3A is a schematic elevation view of an example of a single surface-attached structure 108 according to some embodiments. As described above, the surface-attached structure 108 includes a fixed end 342 attached to an underlying surface 320 at an attachment site, and an opposing free end 344. As described above, the surface 320 may be an inside surface of a flow cell (or chamber thereof), or may be a substrate that is attachable to another surface such as that of a flow cell. The surface-attached structure 108 has a length L from the fixed end 342 to the free end 344. The surface-attached structure 108 also has a characteristic dimension D defining the size of the cross-section of the surface-attached structure 108 that lies in the plane orthogonal to the axis of the length L. The surface-attached structure 108 has a flexible body 346. For example, a dominant portion of the surface-attached structure 108 may be composed of a flexible material. Consequently, the surface-attached structure 108 is movable through space in generally any direction except at the fixed end 342. Thus, the surface-attached structure 108 may be characterized as being movable relative to its attachment site, or fixed end 342.

FIG. 3A schematically illustrates an example of movement of the surface-attached structure 108 by illustrating the surface-attached structure 108 at three different positions A, B, and C. Position A corresponds to an upright position of the surface-attached structure 108. In the upright position, the surface-attached structure 108 may extend to a maximum height above the surface 320 equal to the length L. In the present example, the upright position corresponds to a nominal position at which the surface-attached structure 108 is in a non-deflected state. In other embodiments, however, the surface-attached structure 108 may be fabricated such that it is nominally or inherently bent to some degree in while in its non-deflected state, i.e., in the absence of an applied deflecting force. In response to an appropriately oriented deflecting force, the surface-attached structure 108 may be moved to various other positions relative to position A, such as to position B and/or position C. At position B, the surface-attached structure 108 has generally been rotated clockwise about an axis passing through the drawing sheet. At position C, the surface-attached structure 108 has generally been rotated counterclockwise about the same axis. It will be understood that positions B and C are but a few examples of deflected positions attainable by the surface-attached structure 108. Generally, the surface-attached structure 108 may rotate about any axis relative to its attachment site or fixed end 342. Moreover, generally no limitation is placed on the range of movement of the surface-attached structure 108. In one example, the range of movement may be defined by the angular position of the free end 344 relative to the axis of rotation. For example, positions B and C may correspond to +/−45 degrees of rotation, respectively, in the plane of the drawing sheet. Depending on the composition, length, and characteristic dimension (or aspect ratio, i.e., ratio of length to characteristic dimension, or L:D) of the surface-attached structure 108, its maximum range of movement in a given plane may be more or less than 45 degrees.

As described above, the surface-attached structure 108 includes a metallic component 348 disposed on or in the flexible body 346, which enables movement of the surface-attached structure 108 to be actuated or induced through application of a magnetic or electric field. In the illustrated embodiment, the metallic component 348 is provided in the form of a continuous layer disposed on a selected region of the flexible body 346. As illustrated, the region at which the metallic component 348 is located may be at or near the free end 344 and thus at an appreciable distance from the fixed end 342. This configuration may enhance the responsiveness of the surface-attached structure 108 to an applied magnetic or electric field.

Generally, when the magnetic or electric field is applied, the surface-attached structure 108 experiences a torque that works to align the dominant axis of the surface-attached structure 108 with the magnetic or electric field. The operating parameters of the magnetic or electric field may be set, varied, or adjusted as needed to control movement of the surface-attached structure 108 in a desired manner. As examples, the strength of the magnetic or electric field may determine the extent to which the surface-attached structure 108 is deflected from its nominal, non-deflected state. The strength of the magnetic or electric field may be adjusted to move the surface-attached structure 108 from, for example, position B to some other position between position A and the surface 320. The spatial orientation (as represented by field lines, for example) or polarity of the magnetic or electric field may determine the direction in which the surface-attached structure 108 is deflected, for example to position B or position C. The ON/OFF state of the magnetic or electric field may control whether the surface-attached structure 108 is deflected or not. The magnetic or electric field may be applied once to move the surface-attached structure 108 to position B, for example, and maintained in the ON state for a period of time to hold the surface-attached structure 108 at position B for that period of time. The magnetic or electric field may then be removed to release the surface-attached structure 108, whereby due to its elasticity, the surface-attached structure 108 returns to its non-deflected state. The magnetic or electric field may be cycled between ON and OFF states, or between high-strength and low-strength states, to oscillate the position of the surface-attached structure 108 at a desired frequency, for example between position A and position B. The orientation or polarity of the magnetic or electric field may be cycled to alternate the direction in which the deflecting force is positively or actively applied, for example to oscillate the surface-attached structure 108 between position B and position C. In some embodiments, the magnetic or electric field may be rotated to change the axis about which the surface-attached structure 108 rotates, or to cause the surface-attached structure 108 to gyrate relative to its attachment site or fixed end 342, e.g., gyrate about the axis of position A or other non-deflected position.

In some embodiments, for a given fluid and fluid flow rate, the surface-attached structure 108 may be flexible enough to deflect in response to fluid flow without the assistance of a magnetic or electric field—that is, movement of the surface-attached structure 108 may be actuated by the fluid itself. In such embodiments, a magnetic or electric field may be applied to hold the surface-attached structure 108 at a desired position (e.g., position A, B, or C), in resistance to the force imparted by the flowing fluid, for a desired period of time. The strength of the magnetic or electric field may be varied as desired to allow the surface-attached structure 108 to move to a different position or to oscillate the surface-attached structure 108.

Figure 3B:
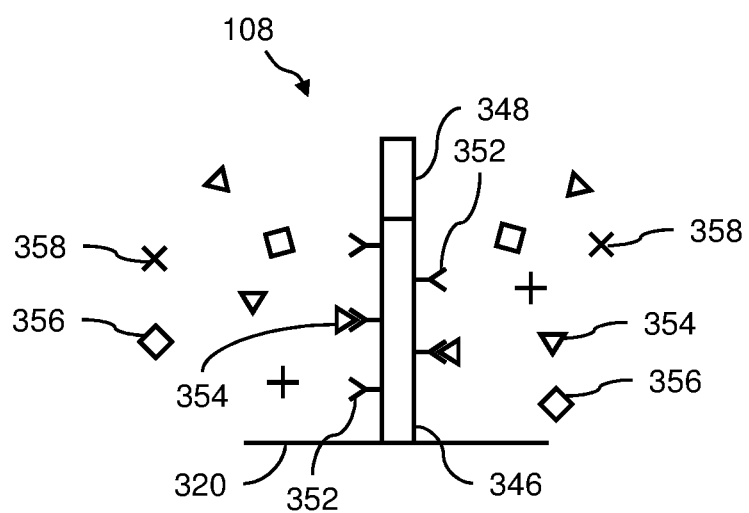
FIG. 3B is a schematic elevation view of another example of the surface-attached structure according to some embodiments.

FIG. 3B is a schematic elevation view of another example of the surface-attached structure 108 according to some embodiments. The surface-attached structure 108 includes a binding agent 352 disposed on or integrated with the outer surface of the surface-attached structure 108 (e.g., the outer surface of the flexible body 346). Generally, no limitation is placed on the manner in which the binding agent 352 is disposed on or integrated with the outer surface of the surface-attached structure 108. As examples, the binding agent 352 may be surface-immobilized by a suitable functionalization technique, applied as a coating, etc. The binding agent 352 may be configured for binding to a target present in a fluid that is brought into contact with the binding agent 352, such as by flowing a fluid sample through the interior of a flow cell as described herein. The binding agent 352 may have a specific affinity for the target of interest. For example, schematically illustrates three different components of a fluid sample, a target 354 and two different "non-targets" 356 and 358. The target 354 readily binds to the binding agent 352, whereas the non-targets 356 and 358 do not. Thus, a surface-attached structure 108 according to such embodiments enables a target 354 to be extracted or isolated from a fluid, specifically by binding or capturing the target 354 as the comes into contact with or close proximity to the binding agent 352. Providing an array of such surface-attached structures 108 in a flow cell as described above may enhance binding efficiency (or capture yield) and the ability to process substantial volumes of fluid in this manner. Generally, the binding agent 352 may be any of the binding agents noted earlier in this disclosure. As one non-limiting example, the binding agent 352 may be avidin or streptavidin, which is capable of conjugation with any biotin-functionalized molecule desired to be captured.

In some embodiments, the binding agent 352 may be disposed on or integrated with one or more inside surfaces of a chamber of a flow cell, which may be the same chamber in which surface-attached structures 108 are provided (e.g., the inside surface 120 shown in FIGS. 1A and 1B). In some embodiments, the binding agent 352 may be disposed on or integrated with both the surface-attached structures 108 (as shown in FIG. 3B) and the inside surface(s) of a chamber.

In some embodiments, the binding agent 352 may be a sequence of binding agents. As one non-limiting example, the surface-attached structure 108 may be functionalized with the following sequence: avidin-biotin-DNA oligo-avidin-biotin-antibody. In this case a target cell, for example, may be captured by the antibody. The target cell may thereafter be released by, for example, a release agent effective for digesting the oligo.

In some embodiments, the outer surfaces of the surface-attached structures 108, or the inside surface of an associated chamber of a flow cell, or both the outer surfaces and the inside surface, are chemically pacified to suppress non-specific binding (or non-specific adsorption (NSA)) and/or contact-activation of clotting. For example, such surfaces may be pacified with a surfactant such as a TWEEN® (polysorbate) surfactant or Triton surfactant, n-Dodecyl-D-maltoside (DDM), etc.

While the schematic illustration of FIG. 3B might suggest the use of a direct binding assaying technique, it will be understood that FIG. 3B illustrates one example of an assaying technique that may be utilized to capture targets from a fluid sample. Other techniques may be utilized such as, for example, competitive assays, inhibition assays, sandwich assays, etc., as appreciated by persons skilled in the art.

Figure 4:
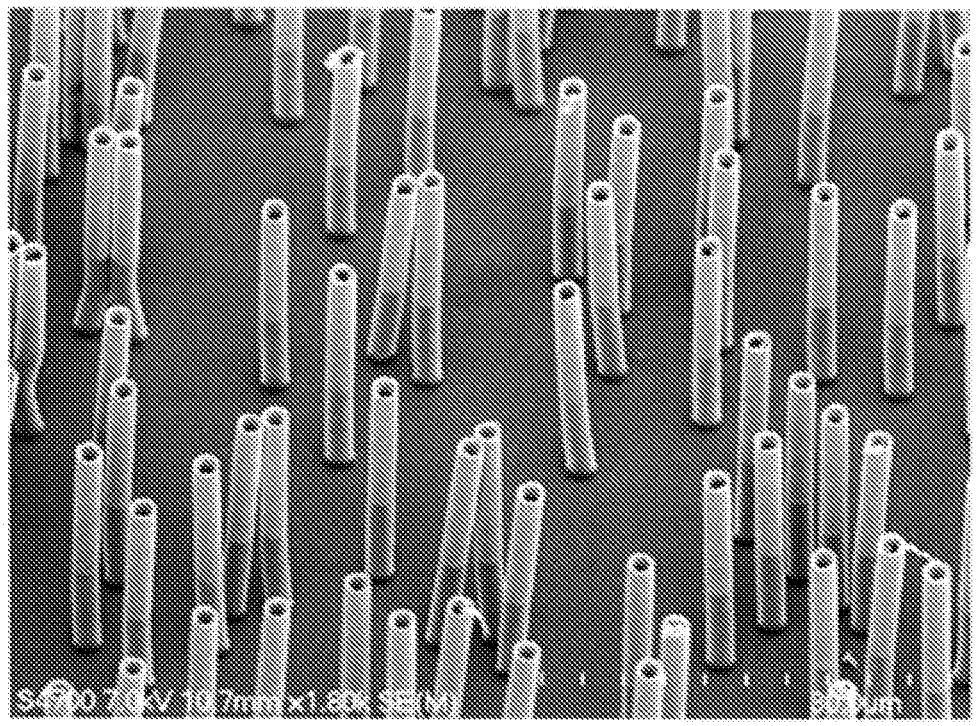
FIG. 4 is a scanning electron micrograph (SEM) of an example of an array of surface-attached structures attached to a substrate according to one embodiment.

FIG. 4 is a scanning electron micrograph (SEM) of an example of an array of surface-attached structures attached to a substrate according to one embodiment. The outer surface of the flexible body of each surface-attached structure is a dark shade, and the outer surface of the metallic component is a lighter shade. In this example, the surface-attached structures were fabricated as described by Judith et al., *Micro-elastometry on whole blood clots using actuated surface-attached posts (ASAPs)*, Lab Chip, Royal Society of Chemistry (2015), DOI: 10.1039/c4lc01478b, the entire content of which is incorporated by reference herein. The surface-attached structures each were fabricated as a core-shell structure in which a nickel shell (metallic component) encapsulates the upper region of a polydimethylsiloxane (PDMS) core (flexible body). A polycarbonate track-etched membrane was utilized as a mold for the core-shell structures. First, the nickel shells were created by coating one side of the track-etched membrane with a 200 nm thick layer of gold that serves as the cathode for electrodeposition of nickel into the pores of the track-etched membrane. Electrodeposition was performed in an electrolytic cell with an all-sulfate plating bath. Upon completion, the nickel containing track-etched membrane was rinsed with deionized water and dried. The cores of the structures were made by filling the membrane with PDMS at a 10:1 base to cross-linker ratio. Prior to curing the PDMS, a 22×22 mm glass coverslip was pressed into the uncured PDMS to provide a rigid substrate for the array. After curing the PDMS, the gold layer was removed using a nickel-compatible gold etchant, and the surface-attached structures were released by dissolving the track-etched membrane using dichloromethane. The released surface-attached structures were then stored in ethanol until they were dried using a critical point drier. The PDMS posts had an elastic modulus of approximately 1 megapascal (MPa) and were able to be bent in response to a magnetic field generated by a soft iron electromagnet.

The array of surface-attached structures shown in FIG. 4 was incorporated into a flow cell similar to the flow cell 100 described above and illustrated in FIGS. 1A and 1B. In this example, and referring to FIGS. 1A and 1B, the glass coverslip corresponds to the first layer 124, a MYLAR® (biaxially-oriented polyethylene terephthalate, or BoPET) lid corresponds to the second layer 126, a double-sided adhesive spacer corresponds to the third layer 128, and an underlying layer of PDMS formed during fabrication of the surface-attached structures 108 corresponds to the substrate 136. The length (or height) of the surface-attached structures 108 was about 23 µm, and the height of the chamber interior above the surface-attached structures 108 was about 200 µm.

It will be understood that the method described above in conjunction with FIG. 4 for fabricating surface-attached structures and an associated flow cell is but one example. Other examples of fabricating surface-attached structures are disclosed in U.S. Pat. No. 8,586,368, the entire content of which is incorporated by reference herein. More generally, any method of fabrication that produces surface-attached structures having structures, geometry, properties and functionalities as disclosed herein may be utilized.

According to an aspect of the present disclosure, a flow cell with surface-attached structures as described herein may be utilized in carrying out a method for extracting a target from a sample. In some embodiments, the method may include flowing a target-containing sample through the flow cell and into contact with the surface-attached structures disposed in the flow cell. While flowing the sample, the flow cell isolates targets of the sample from a remaining portion of the sample. The flow cell may be configured to implement various types of isolation mechanisms. One mode of isolation entails binding the targets to a binding agent disposed in the flow cell, as described herein.

Figure 5:
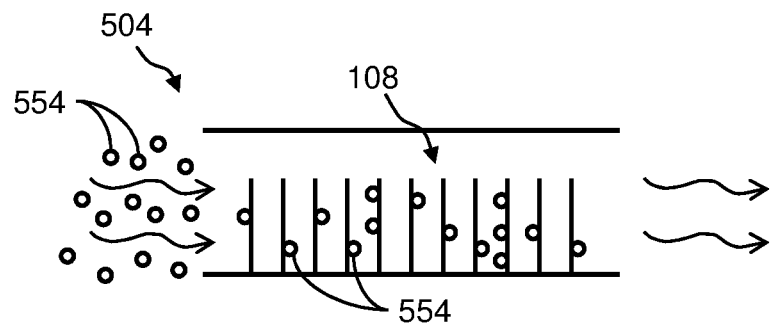
FIG. 5 is a schematic view of an example of a chamber of a flow cell, wherein the chamber is configured for extracting or isolating a target from a fluid sample according to one embodiment.

FIG. 5 is a schematic view of an example of a chamber 504 of a flow cell, wherein the chamber 504 is configured for extracting or isolating a target 554 from a fluid sample according to one embodiment. FIG. 5 is a lengthwise view of the chamber 504, such that fluid generally flows from a fluid inlet on the left to a fluid outlet on the right. The fluid flow is schematically depicted by curved arrows at different elevations on the left and on the right. The fluid sample may include any number of other components in addition to the target 554 of interest. In this embodiment, the surface-attached structures 108, the inside surface of the chamber 504, or both, include a binding agent specific to the target 554, as described above. As the fluid sample flows through the chamber 504 and comes into contact with the surface-attached structures 108 (and/or the inside surface), the targets 554 (or at least a significant fraction of the targets 554) are captured by the surface-attached structures 108 (as illustrated) and/or by the inside surface, depending on the location(s) of the binding agent. As a result, the captured (bound) targets 554 are removed from the fluid sample as illustrated.

Subsequently, the captured (bound) targets 554 may be released from the binding agent, thereby allowing the released targets 554 to be flowed out from the chamber 504, such as by being carried by a different fluid flowed into the chamber 504 behind the fluid sample. Generally, any release mechanism effective for overcoming the bond or affinity between the targets 554 and the binding agent may be utilized, and may depend on the types of target 554 and binding agents involved in a given application. In some embodiments, a fluid functioning as (or containing) a release agent may be flowed behind the fluid sample and into contact with the bound targets 554. Examples of such release agents include, but are not limited to, a chemical lysing agent, a pH cell lysing agent, an enzymatic liquefaction agent, and a solvent. In other embodiments, photolysis may be performed by irradiating the bound targets 554 with photons under conditions effective for inducing photolysis (e.g., wavelength, intensity, etc.). In other embodiments, the release modality may entail applying a shear force to the bound targets 554 at a magnitude effective for unbinding the bound targets. As one example of shearing, a shearing liquid may be flowed through the flow cell behind the fluid sample at a flow rate effective for releasing the bound targets 554 by shearing. The shearing liquid may be water or another common solvent, which in some embodiments may be flowed at a flow rate significantly higher than the flow rate of the preceding fluid sample. Alternatively, the liquid may have a viscosity high enough at a given flow rate to enhance the shearing action imparted to the bound targets 554. As another example of shearing, a magnetic or electric field may be applied to the flow cell to actuate movement of the surface-attached structures (as described above in conjunction with FIG. 3B) at a speed effective for releasing the bound targets 554 by shearing. Still other embodiments may utilize a combination of two or more of the foregoing release mechanisms.

In some embodiments, additional measures may be taken to enhance the release functionality. One example is electroporation, which may be implemented by applying a DC or AC voltage of appropriate magnitude/amplitude across the chamber interior.

The extraction or isolation of targets 554 from a fluid sample may be useful in a variety of applications. In some embodiments, the target 554 is an analyte having an attribute or property for which measurement is desired, or for which detection of its presence in the fluid sample is desired. The chamber 504 may be useful for capturing rare analytes from fluid samples having a wide range of volumes, as the isolation modality provided by the chamber 504 may be effective for concentrating rare analytes. After isolating the analyte (target 554) in the chamber 504, the isolated analyte may be released and eluted from the chamber 504 to any desired destination. For example, the analyte may be flowed to a collection receptacle or other type of collection site. The receptacle may then be decoupled from the system to enable the analyte to be transferred to an off-line analytical instrument, storage site, or other destination. In other embodiments, the receptacle may be part of an on-line analytical instrument or other type of sample processing device positioned downstream from the chamber 504.

In other embodiments, the target 554 may be an unwanted component of the fluid sample. For example, the target 554 may be a toxin, pathogen, carcinogen, or the like, or may interfere with or suppress a subsequent analysis, detection, or reaction to be performed on the fluid sample, or may contribute to the background noise of a measurement signal to be generated from the fluid sample, etc. Thus, the chamber 504 may be useful for removing the target 554 for the purpose of sample purification or cleanup, which may be analogous to techniques that utilize conventional sorbents and stationary phases such as, for example, solid phase extraction (SPE), preparative chromatography, and the like.

After isolating the targets 554 from the fluid sample, the purified/cleaned up fluid sample may be flowed or transported to any desired destination such as a collection container, analytical instrument, other type of sample processing device, etc., as described above. In some embodiments, after a prescribed period of time has elapsed during which the fluid sample flows through the chamber 504, the fluid line downstream from the fluid outlet of the chamber 504 may be switched to a path leading to a collection site for the purified/cleaned up fluid sample. For a given application, this period of time may be determined empirically, or by analyzing the presence or concentration of residual target 554 in the fluid sample. The latter may be performed off-line at one or more intervals, or a system associated with the chamber 504 may be configured for monitoring the fluid sample on-line (intermittently or continuously) as it elutes from the chamber 504. After removing the target 554 (or reducing its concentration to a desired level), the isolated target 554 may be released and eluted from the chamber 504 via a release mechanism such as described herein, and transferred to waste or another desired destination.

In some embodiments, while the fluid sample flows through the chamber 504, a magnetic or electric field may be applied to the flow cell to actuate movement of the surface-attached structures 108 in an oscillating or reciprocating manner to increase a time-averaged cross-section of the surface-attached structures 108. This oscillation or reciprocation may increase the likelihood of desired binding events occurring.

In other embodiments, a flow cell as described herein may be configured to implement other types of isolation mechanisms as an alternative to, or in addition to, mechanisms based on binding or affinity.

Figure 6:
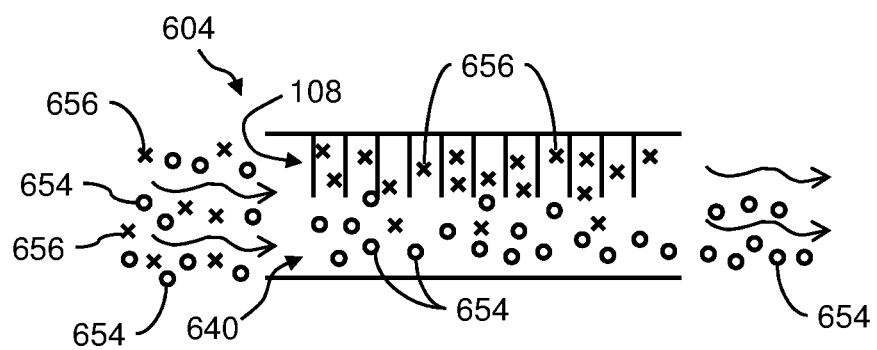
FIG. 6 is a schematic view of an example of a chamber of a flow cell, wherein the chamber is configured for extracting or isolating a target according to another embodiment.

FIG. 6 is a schematic view of an example of a chamber 604 of a flow cell, wherein the chamber 604 is configured for extracting or isolating a target 654 according to another embodiment. Similar to FIG. 5, FIG. 6 is a lengthwise view of the chamber 604, such that fluid generally flows from a fluid inlet on the left to a fluid outlet on the right. The fluid flow is schematically depicted by curved arrows at different elevations on the left and on the right. The fluid sample may include any number of other components in addition to the target of interest. As an example, FIG. 6 schematically illustrates two different components: a first component 654 and a second component 656. Depending on the embodiment, either or both components 654 and 656 may be a target or analyte of interest. In the illustrated embodiment, the surface-attached structures 108 are attached to the top inside surface of the chamber such that a structure-free region 640 is below the surface-attached structures 108, which may facilitate certain applications as described below. In other embodiments, the surface-attached structures 108 may be attached to the bottom inside surface or to both the top and bottom inside surfaces as described herein.

In one embodiment, the chamber 604 is configured for separating the first component 654 from the fluid sample by implementing a filtering or size exclusion technique, which may be analogous to size exclusion chromatography (SEC) but without the use of porous beads. In this case, the first component 654 may be considered to be the target or analyte. The inter-structure spacing of the array of surface-attached structures 108 is set such that as the fluid sample flows through the chamber 604, the first components 654 cannot pass through the array of surface-attached structures 108, i.e., cannot pass between adjacent surface-attached structures 108. Instead, as illustrated the first components 654 are forced to flow through the structure-free region 640 below the surface-attached structures 108, while other components such as the second components 656 are small enough to flow through the array of surface-attached structures 108. Because the first components 654 travel through a shorter path length and/or fluid volume compared to the second components 656, the first components 654 and the second components 656 become separated in time and space. Consequently, a substantial fraction of the first components 654 elute from the chamber 604 first, i.e., before the second components 656 elute from the chamber 604, as schematically depicted at the fluid outlet in FIG. 6. In this manner, the first components 654 become isolated from the second components 656 (and possibly one or more other components of the fluid sample) in a manner analogous to chromatographic bands or peaks.

Because the first components 654 elute from the chamber 604 separately, they may be collected separately. Fluidics downstream from the fluid outlet may be configured to route the first components 654 to a desired receptacle and then, after collection of the first components 654 is complete, switch the fluid flow to another receptacle to receive the remaining portion of the fluid sample. The respective operations of such fluidics and the chamber 604 may be coordinated in a number of ways, as appreciated by persons skilled in the art. For example, the operation of a flow-switching device such as a valve may be synchronized with the operation of the chamber 604. The duration of fluid flow through chamber 604 required for adequate isolation of the first components 654 may be determined empirically, or through use of an appropriate detector, etc.

In another embodiment, the chamber 604 is configured for separating the first component 654 from the fluid sample by a technique referred to herein as density separation. In this case, the first component 654 is a denser particle in comparison to other components of the fluid sample. The flow rate and the length of the chamber 604 are selected such that as the fluid sample flows through the chamber 604, the higher-density first components 654 tend to settle or diffuse toward the bottom inside surface such that all or a substantial fraction of the first components 654 flow through the structure-free region 640. To achieve this effect, the flow rate may be relatively low in comparison to other methods disclosed herein. Typically, the shorter the length of the chamber 604, the lower the flow rate should be in order to achieve the density separation effect effectively.

In some embodiments, the mechanism of isolation may be a combination of filtering/size exclusion and density separation.

The isolation techniques described above in conjunction with FIG. 6 may be useful for separating first components 654 that are large particles relative to other components of the fluid sample. For example, the fluid sample may be whole blood and the first components 654 may be intact red blood cells (erythrocytes). As more general examples, the fluid sample may be a colloid in which the first components 654 are the dispersed phase, or a suspension in which the first components 654 are the suspended solids.

In some embodiments, the chamber 604 may also include a binding agent disposed on or integrated with the surface-attached structures 108, the inside surface of the chamber 604, or both, as described elsewhere in the present disclosure. The binding agent may have a specific affinity for a component other than the first component 654, such as the illustrated second component 656. The added modality of binding may be useful for enhancing isolation of the first component 654, providing multi-target isolation, or any other purpose found to be useful.

In some embodiments, the first component 654 may be an unwanted component, in which case isolation of the first component 654 may be done for the purpose of sample purification or cleanup.

In another embodiment, a flow cell as described herein may be configured to isolate a target by trapping the target in the array of surface-attached structures 108. The target may be trapped by preventing the target from passing between neighboring surface-attached structures 108. This may be accomplished by setting an appropriate inter-structure spacing between the surface-attached structures 108. The inter-structure spacing may be adjusted by applying a magnetic or electric field to the flow cell to actuate movement of the surface-attached structures 108 as described herein. After trapping the target for a desired period of time, the target may be released by applying a magnetic or electric field to the flow cell to actuate movement of the surface-attached structures 108, specifically to increase the inter-structure spacing enough for the previously trapped target to be able to pass through the surface-attached structures 108 and elute from the flow cell.

In various embodiments, a magnetic or electric field may be applied to the flow cell to actuate movement of the surface-attached structures 108. The surface-attached structures 108 may be moved to achieve various effects. In addition to those described elsewhere in the present disclosure, examples of effects achieved by moving the surface-attached structures 108 include, but are not limited to, adjusting or varying an inter-structure spacing between the surface-attached structures 108, preventing or disrupting clogging of sample material between the surface-attached structures 108, and/or preventing or disrupting non-specific binding of sample material on the surface-attached structures 108. The effect achieved by moving the surface-attached structures 108 may be optimized by varying one or more parameters such as, for example, flow rate, inter-surface spacing (density of the surface-attached structures 108), and the frequency oscillation/reciprocation.

Figure 7:
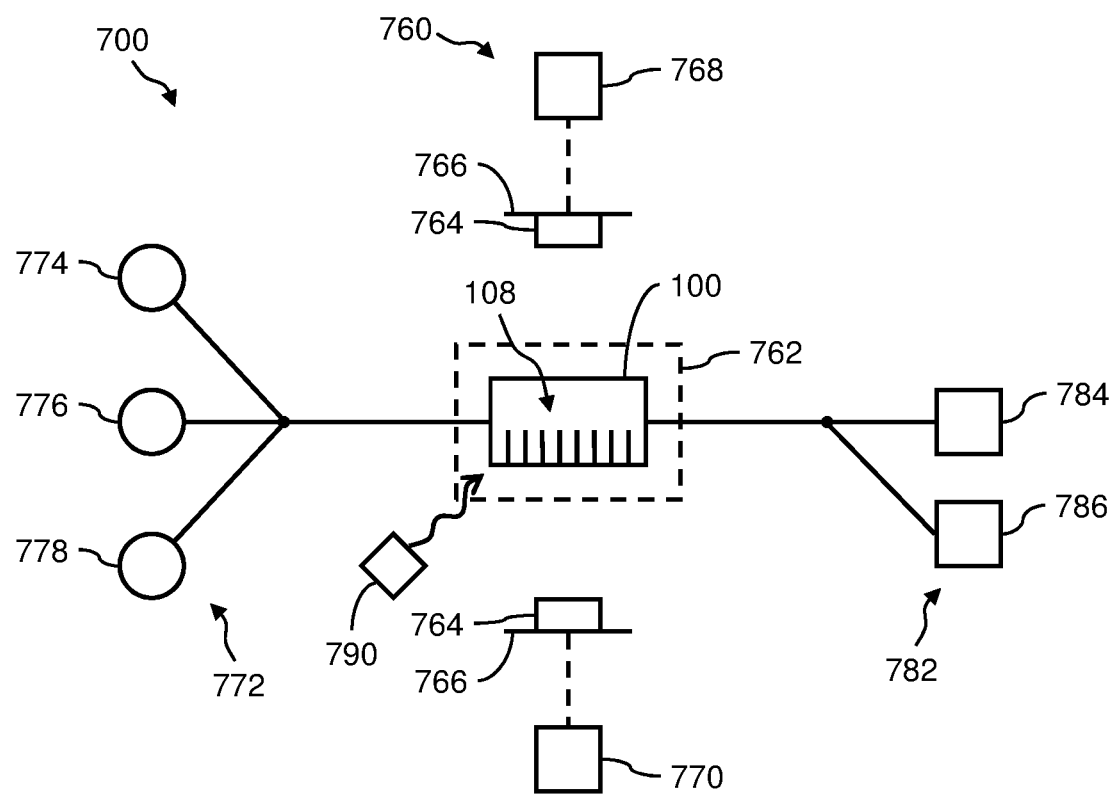
FIG. 7 is a schematic view of an example of a target extraction system according to some embodiments.

FIG. 7 is a schematic view of an example of a target extraction system 700 according to some embodiments. The target extraction system 700 may include a flow cell 100 according to any of the embodiments disclosed herein, and a driver 760 configured for applying a magnetic or electric field to the interior of the flow cell 100 to actuate movement of the surface-attached structures 108 as described herein. In some embodiments, the target extraction system 700 may further include a housing 762 configured for removably receiving the flow cell 100. In such case, the flow cell 100 may be configured as a cartridge and the housing 762 may be configured as (or may include) a cartridge support or receptacle. By this configuration, the flow cell 100 after use may be replaced with a new or cleaned or sterilized flow cell or with a differently configured flow cell.

Generally, devices and methods for generating and controlling magnetic and electric fields are known to persons skilled in the art, and thus the driver 760 will be described herein only briefly as necessary for facilitating an understanding of the presently disclosed subject matter. The particular configuration of the driver 760 depends on whether it applies a magnetic field or an electric field. Generally, the driver 760 includes a field generator 764. The field generator 764 may be mounted to a suitable field generator support 766. The field generator support 766 may hold the field generator 764 in a position relative to the flow cell 100 at which the field generator 764 is able to apply a magnetic or electric field of a desired strength and orientation to the surface-attached structures 108. In embodiments applying a magnetic field, the field generator 764 may include one or more magnets of a suitable size and shape. The magnets may be permanent magnets, electromagnets, or a combination of both types. In embodiments applying an electric field, the field generator 764 may include one or more electrodes of a suitable size and shape. When the field generator 764 includes only a single magnet or electrode, the magnetic or electric field may be established primarily between that magnet or electrode and the metallic components of the surface-attached structures 108. The field generator 764 may include additional magnets or electrodes as needed for generating a magnetic or electric field having a desired spatial orientation relative to the surface-attached structures 108.

In embodiments providing electromagnets or electrodes, the driver 760 may further include a power source 768 in electrical communication with the electromagnets or electrodes. The power source 768 may be configured to supply variable electrical power to the electromagnets or electrodes. In various embodiments, the driver 760 may be configured for varying a parameter of the magnetic or electric field, such as magnetic or electric field strength, magnetic or electric field direction (orientation), and/or a frequency at which the magnetic or electric field is cycled between ON and OFF states or high-strength and low-strength states.

In some embodiments all or part of the driver 760, such as the field generator 764 and any associated field generator support 766, may be movable relative to the flow cell 100 (and the housing 762, if provided). By this configuration, the position of the field generator 764 may be adjusted to adjust the orientation of the applied magnetic or electric field. Alternatively or additionally, the field generator 764 (particularly in the case of permanent magnets) may be oscillated or reciprocated between different positions to cause the surface-attached structures 108 to oscillate or reciprocate, as described above in conjunction with FIG. 3A. For example, the field generator 764 may be rotated about the longitudinal axis of the flow cell 100. In other embodiments, power may be supplied at different magnitudes to different electromagnets or electrodes to adjust and/or oscillate the orientation of the magnetic or electric field.

In some embodiments, the driver 760 may include an actuator coupled (e.g., mechanically) to the magnets or electrodes of the field generator 764 to actuate movement of the magnets or electrodes. The actuator may include a motor 770 for powering the movement, and an appropriate linkage (e.g., shaft) coupled between the motor 770 and the magnets or electrodes, as appreciated by persons skilled in the art. The actuator may move the magnets or electrodes to adjust or oscillate their positions, such as by rotation about the longitudinal axis of the flow cell 100. In the case of permanent magnets, the actuator may translate the permanent magnets toward or away from the flow cell 100 (and the housing 762, if provided) to adjust the magnetic field strength applied to the surface-attached structures 108.

When coupled into the target extraction system 700, the flow cell 100 may be operated or utilized to process sample fluid in accordance with any of the methods disclosed herein. While a fluid sample is flowing through the flow cell 100, the driver 760 may actuate movement of the surface-attached structures 108 in accordance with any of the methods disclosed herein.

In some embodiments, the target extraction system 700 may include a fluid supply source 772 configured for flowing a fluid to the fluid input of the flow cell 100. The fluid supply source 772 may include one or more different fluid supply sources communicating with respective fluid lines (e.g., tubing). For example, the fluid supply source 772 may include a sample source 774 configured for flowing a target-containing sample to the fluid input. The fluid supply source 772 may also include one or more processing fluid sources 776 and 778 configured for flowing other fluids to the fluid input. The processing fluid sources 776 and 778 may include, for example, a source of a release agent or a shearing fluid effective for releasing targets bound to a surface inside the flow cell 100 (or otherwise captured or trapped in the flow cell 100) as described elsewhere herein, and/or a source of rinsing agent effective for rinsing/washing the flow cell 100 so as to purge the flow cell 100 of residual components from a previous operation of the flow cell 100 and prepare the flow cell 100 for the next operation.

In some embodiments, the target extraction system 700 may include a fluid receptacle 782 configured for receiving processed fluid from the fluid output of the flow cell 100. The fluid receptacle 782 may include one or more different fluid receptacles communicating with respective fluid lines (e.g., tubing). For example, the fluid receptacle 782 may include one or more fluid receptacles 784 configured for collecting one or more fluids carrying respective targets isolated by the flow cell 100. In some embodiments, the fluid receptacle(s) 784 may be part of or communicate with an analytical instrument or other type of sample processing device as described herein. The fluid receptacle 782 may also include one or more fluid receptacles 786 for receiving one or more different types of processed fluid other than a fluid carrying targets. For example, one or more of the fluid receptacles 786 may be configured for receiving purified or cleaned up fluid samples. As other examples, one or more of the fluid receptacles 786 may serve generally as waste receptacles for receiving spent process fluids such as release agents, shearing fluids, and/or rinsing agents. As another example, one or more of the fluid receptacles 786 may serve as the destination for fluids flowed through the target extraction system 700 for pre-operation purposes, such as for purging the fluid lines of bubbles, priming the fluid lines, etc.

FIG. 7 schematically depicts different fluid input lines coupled to a common fluid input line leading to the fluid inlet of the flow cell 100, and different fluid output lines branching off from a common fluid output line leading from the fluid outlet of the flow cell 100. It will be understood that such an arrangement is but one example of many possible configurations of the fluid circuitry that may be provided by the target extraction system 700. In addition, it will be understood that in practice, other fluidic components and devices may be included as necessary for realizing different applications, such as valves (proportional valves, multi-port valves, etc.), flow regulators, pressure regulators, temperature regulators, flow path switches/selectors, flow restrictors, sample loops, etc., all as appreciated by persons skilled in the art. Moreover, depending on the embodiment, fluid flow through the flow cell 100 may be active (e.g., by employing a pump upstream of or downstream from the flow cell 100, other means for actively creating a pressure differential, etc.) or passive (e.g., by capillary action, wicking, gravity-assist, electrokinetics, etc.). In some embodiments, the reservoirs or containers associated with the fluid supply source 772 may be integral parts of syringes (syringe pumps).

In some embodiments, the target extraction system 700 may include a photon source or light source 790 and associated optics for generating photons and directing the photons to the surface-attached structures 108 to perform photolysis as described above. In this case, all or a part of a wall of the flow cell 100 exposed to at least a portion of the interior of the flow cell 100 may be optically transparent to the wavelength(s) of the photons. The photon source 790 may be positioned, for example, in the housing 762. Examples of photon sources include, but are not limited to, broadband light sources (e.g., flash lamps), light-emitting diodes (LEDs), laser diodes (LDs), and lasers, any of which may be wavelength-filtered if desired. In some embodiments, the target extraction system 700 may include a heating device of any suitable type (not shown) configured to control fluid temperature in the flow cell 100. The heating device may be positioned, for example, in the housing 762 proximate to the flow cell 100. In some embodiments, the photon source 790 or another photon source may be utilized for infrared (IR) heating of the fluid flowing through the flow cell 100.

When coupled into the target extraction system 700, the flow cell 100 may be operated or utilized to process sample fluid in accordance with any of the methods disclosed herein. While a fluid sample is flowing through the flow cell 100, the driver 760 may actuate movement of the surface-attached structures 108 in accordance with any of the methods disclosed herein. The fluid supply source 772 and the receptacle 782 may be utilized as needed to supply and receive fluids in accordance with any of the methods disclosed herein.

Figure 8:
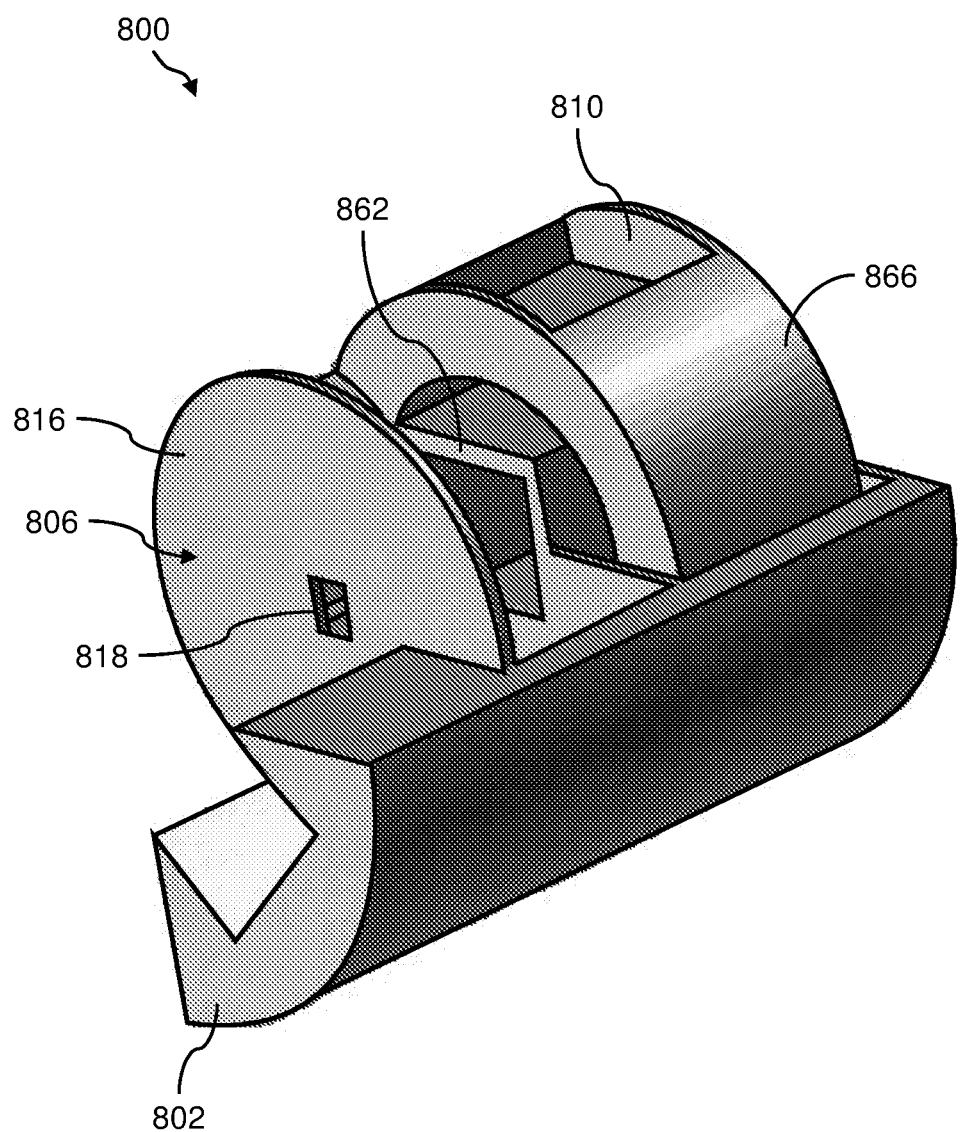
FIG. 8 is a perspective view of an example of a target extraction system (or a portion thereof) according to another embodiment.

FIG. 8 is a perspective view of an example of a target extraction system 800 (or a portion thereof) according to another embodiment. The target extraction system 800 may include a stator 802 positioned on an axis, and a rotor 806 that may be rotated about the axis. The stator 802 may include a housing 862 in which a flow cell (not shown) may be removably installed for operation in the target extraction system 800 as described herein. The rotor 806 may serve as the actuator of a driver as described herein. The rotor 806 may include a field generator support 866 configured for supporting one or more magnets. For example, the field generator support 866 may include one or more recesses 810 in which respective magnets may be mounted. In other embodiments, the field generator support 866 may be configured for supporting one or more electrodes. The rotor 806 may also include a shaft support 816 configured for supporting the shaft of a motor (not shown) as described herein. In the illustrated embodiment, the shaft support 816 includes a square aperture 818 that receives a square motor shaft. The shaft support 816 may be mechanically coupled to the field generator support 866, such that the shaft support 816 and the field generator support 866 rotate together about the axis of the housing 862 (and the flow cell disposed therein). The position of the motor may be fixed in space by a suitable mounting arrangement (not shown). Thus, the rotor 806 (including the shaft support 816 and the field generator support 866) may be supported in space by the motor through its fixed mounting arrangement and the interconnection between the motor and the rotor 806 provided by the motor shaft. The stator 802 may be supported independently of the motor and the rotor 806, such that the motion of the rotor 806 is independent of the stator 802 and the mounting arrangement (not shown) of the stator 802. In some embodiments, the motor may provide power for actuating oscillatory rotation of the magnet(s) as described herein. That is, the rotational power generated by the motor is transferred to the magnet(s) via the motor shaft, shaft support 816, and field generator support 866.

Generally, the stator 802 and the rotor 806 may be fabricated by any suitable technique. In some embodiments, the stator 802 and the rotor 806 may be fabricated by a three-dimensional (3D) printing technique as appreciated by persons skilled in the art. In some embodiments, the stator 802 and the rotor 806 may be incorporated into the target extraction system 700 described above and illustrated in FIG. 7.

Figure 9:
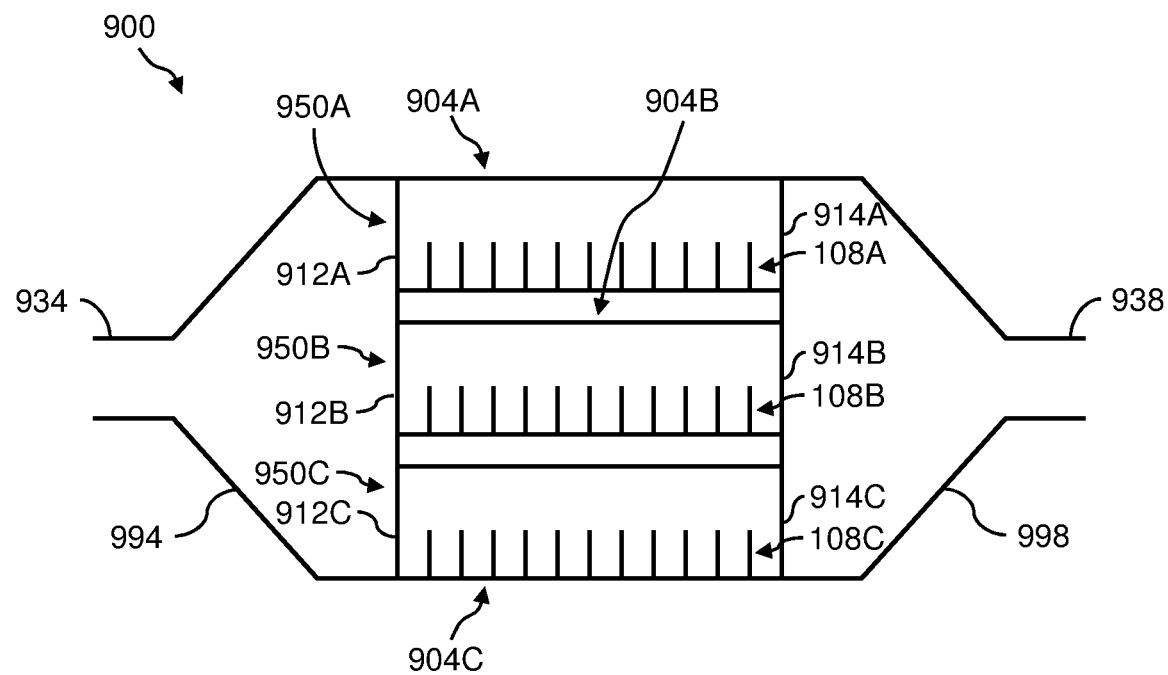
FIG. 9 is a schematic elevation view of an example of a flow cell according to an embodiment in which the flow cell includes a plurality of flow cell units arranged in parallel.
Figure 10:
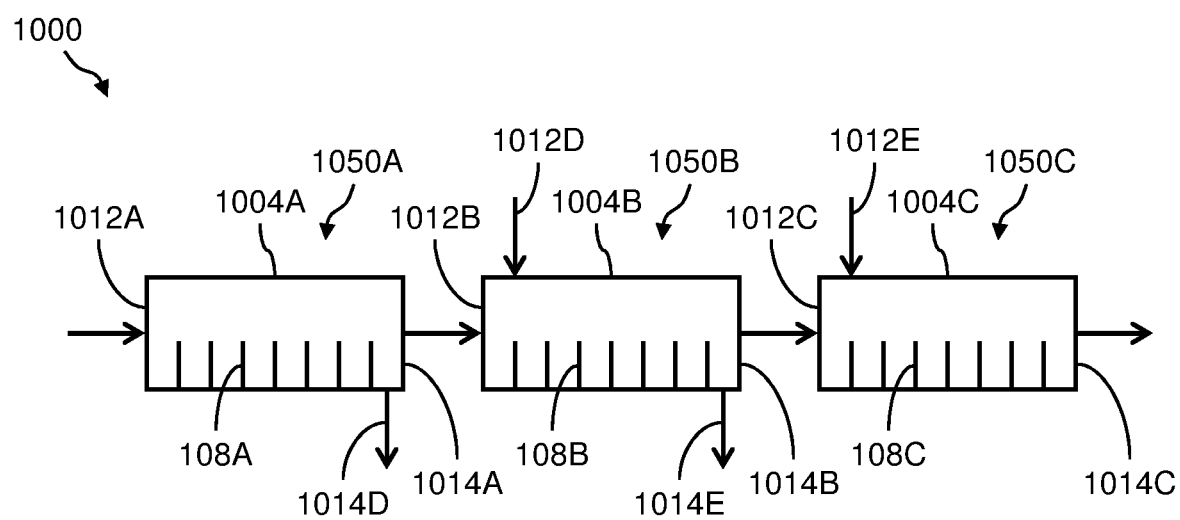
FIG. 10 is a schematic elevation view of an example of a flow cell according to an embodiment in which the flow cell includes a plurality of flow cell units arranged in series.

In some embodiments, a flow cell as described herein may in effect be partitioned into a plurality of flow cell units, with each flow cell unit including a chamber and a plurality of surface-attached structures as described herein. The flow cell units may be arranged in parallel or in series. FIGS. 9 and 10 illustrate examples of arrangements of flow cell units.

Specifically, FIG. 9 is a schematic elevation view of an example of a flow cell 900 according to an embodiment in which the flow cell 900 includes a plurality of flow cell units 950A, 950B, and 950C stacked in parallel. FIG. 9 is a lengthwise view of the flow cell 900, such that fluid generally flows from the left to the right. By example, FIG. 9 illustrates three flow cell units 950A, 950B, and 950C, with the understanding that more or less than three flow cell units 950A, 950B, and 950C may be provided. Each flow cell unit 950A, 950B, and 950C includes a fluid inlet 912A, 912B, and 912C, a fluid outlet 914A, 914B, and 914C, a chamber 904A, 904B, and 904C between the fluid inlet 912A, 912B, and 912C and the fluid outlet 914A, 914B, and 914C, and a plurality of surface-attached structures 108A, 108B, and 108C attached to an inside surface of the chamber 904A, 904B, and 904C. Thus, the flow cell units 950A, 950B, and 950C establish separate, parallel fluid flow paths through the flow cell 900, whereby fluids flowing simultaneously through the different flow paths encounter separate sets of surface-attached structures 108A, 108B, and 108C, respectively.

In some embodiments, the sets of surface-attached structures 108A, 108B, and 108C have the same configuration, e.g., the same inter-structure spacing, the same binding agent (if any), etc. In this case, the multi-unit flow cell 900 may be advantageous for increasing the volumetric capacity of the flow cell 900 without affecting any design considerations or constraints relating to the individual flow cell units 950A, 950B, and 950C. That is, each flow cell unit 950A, 950B, and 950C may be configured in an optimal manner that does not require accounting for the total volumetric capacity desired for the flow cell 900. Any volumetric requirement of the flow cell 900 may be met by providing a sufficient number of flow cell units in the parallel stack. Moreover, providing additional chambers 904A, 904B, and 904C may multiply the surface area to which a given volume of fluid is exposed. For embodiments providing binding agents at internal surfaces of the chambers 904A, 904B, and 904C (e.g., at the surface-attached structures 108A, 108B, and 108C and/or at inside surfaces of the chambers 904A, 904B, and 904C), this configuration may enhance the effectiveness of the binding/capturing functionality of the flow cell 900.

In other embodiments, at least one set of surface-attached structures 108A, 108B, and 108C may be configured differently than the other sets. For example, at least one set may have a different inter-structure spacing, or a different binding agent, etc. As another example, at least one set may have a binding agent while the other sets do not, or at least one set may have no binding agent while the other sets do have binding agents. As another example, at least one chamber 904A, 904B, and 904C may include surface-attached structures while the other chambers 904A, 904B, and 904C do not, or at least one chamber 904A, 904B, and 904C may include no surface-attached structures while the other chambers 904A, 904B, and 904C do include surface-attached structures. The chamber(s) 904A, 904B, and 904C that do not include surface-attached structures may or may not include binding agents at the inside surfaces. Embodiments providing differently configured flow cell units 950A, 950B, and 950C may be useful for isolating more than one type of target from a fluid sample.

In some embodiments, one of the flow cell units 950A, 950B, and 950C may be a reference flow cell unit that is part of a flow path utilized to generate a reference signal utilized for calibration or other purposes. The configuration of the reference flow cell unit may or may not be the same as that of the other flow cell units. The reference flow cell unit may communicate with a separate fluid source, a separate fluid receptacle, or with both a separate fluid source and a separate fluid receptacle.

In some embodiments, one or more of the individual flow cell units 950A, 950B, and 950C may communicate with separate fluid sources and/or separate fluid receptacles. In some embodiments, two or more of the individual flow cell units 950A, 950B, and 950C may communicate with a common fluid source and/or a common fluid receptacle. As illustrated in FIG. 9, in some embodiments all of the individual flow cell units 950A, 950B, and 950C may communicate with a common fluid source and/or a common fluid receptacle. In such embodiments, the flow cell 900 may include a common fluid input port 934 and/or a common fluid output port 938. The flow cell 900 may also include an input manifold 994 or other type of transition between the fluid input port 934 and the fluid inlets 912A, 912B, and 912C, and/or an output manifold 998 or other type of transition between the fluid output port 938 and the fluid outlets 914A, 914B, and 914C.

FIG. 10 is a schematic elevation view of an example of a flow cell 1000 according to an embodiment in which the flow cell 1000 includes a plurality of flow cell units 1050A, 1050B, and 1050C arranged in series. FIG. 10 is a lengthwise view of the flow cell 1000, such that fluid generally flows from the left to the right. By example, FIG. 10 illustrates flow cell units 1050A, 1050B, and 1050C, with the understanding that more or less than three flow cell units 1050A, 1050B, and 1050C may be provided. Each flow cell unit 1050A, 1050B, and 1050C includes a fluid inlet 1012A, 1012B, and 1012C, a fluid outlet 1014A, 1014B, and 1014C, a chamber 1004A, 1004B, and 1004C between the fluid inlet 1012A, 1012B, and 1012C and the fluid outlet 1014A, 1014B, and 1014C, and a plurality of surface-attached structures 108A, 108B, and 108C attached to an inside surface of the chamber 1004A, 1004B, and 1004C. In the illustrated series arrangement, the fluid inlet or the fluid outlet of each flow cell unit 1050A, 1050B, and 1050C communicates with the fluid inlet or the fluid outlet of at least one other flow cell unit 1050A, 1050B, and 1050C.

Generally, the series-arranged multi-unit flow cell 1000 may provide one or more of the same advantages or functions as the parallel-arranged flow cell 900 described above. As in the case of the parallel-arranged flow cell 900, the chambers 1004A, 1004B, and 1004C and corresponding surface-attached structures 108A, 108B, and 108C of the series-arranged flow cell 1000 may be configured the same as or differently from each other.

As shown in FIG. 10, in some embodiments one or more of the flow cell units 1050A, 1050B, and 1050C may include an additional (or auxiliary) fluid inlet (e.g., fluid inlets 1012D and 1012E) and/or an additional (or auxiliary) fluid outlet (e.g., fluid outlets 1014D and 1014E). The additional fluid inlets and fluid outlets may be utilized for various purposes. For example, the additional fluid inlets and fluid outlets may enable fluid flow through the flow cell 1000 to bypass one or more selected flow cell units 1050A, 1050B, and 1050C, thereby imparting a modularity to the flow cell 1000 and facilitating customization for a desired application. The bypassing of a selected flow cell unit may be temporary, such as to enable elution from the additional fluid outlet of a preceding flow cell unit to occur for a period of time before resuming fluid flow into the selected flow cell unit.

As another example, the additional fluid inlets and fluid outlets may facilitate multi-target isolation as may be implemented with differently configured flow cell units 1050A, 1050B, and 1050C. For example, the first flow cell unit 1050A may be configured to capture a first target from a fluid sample containing multiple different targets. After capturing the first targets, the first flow cell unit 1050A may release the first targets into a fluid, and then output the first target-laden fluid through the additional fluid output 1014D. By this configuration, the first targets need not flow through the remaining flow cell units 1050B and 1050C. In a given sample extraction system, this configuration may facilitate the analysis of the first target separately from other targets. The configuration may enhance the effectiveness of the other flow cell units 1050B and 1050C in isolating other targets. For example, the second flow cell unit 1050B may be configured to capture a second target from the same fluid sample, then release the second targets into a fluid, and then output the second target-laden fluid through the additional fluid output 1014E, and so on.

In other embodiments, two or more flow cell units 1050A, 1050B, and 1050C may be configured to capture the same type of target and, after releasing the captured targets, the different fluid outputs may be utilized to flow the target-laden fluid to two or more different fluid receptacles, such as to perform different analyses or reactions on the same target.

To facilitate the use of additional fluid inlets and fluid outlets, valves or other flow regulators (not shown) may be provided in the fluid line between adjacent flow cell units 1050A, 1050B, and 1050C, as appreciated by persons skilled in the art.

In another embodiment, the flow cell units 1050A, 1050B, and 1050C may be configured for performing multi-stage particle sizing. In this embodiment, the inter-structure spacing of the surface-attached structures 108A, 108B, and 108C may be progressively smaller in each flow cell unit 1050A, 1050B, and 1050C. Hence, the largest particles in a fluid sample may be isolated in the first flow cell unit 1050A, followed by intermediate-sized particles in the same fluid sample being isolated in the second flow cell unit 1050B, followed by even smaller particles in the same fluid sample being isolated in the third flow cell unit 1050C.

In some embodiments, the present invention provides surface-attached structures (e.g., micropost arrays) for enhancing flow, circulation, and/or mixing action for analyte capture on a microarray (or analyte capture array, or probe array), and related systems and methods. The surface-attached structures are positioned in relation to the microarray such that actuated motion of the surface-attached structures can be used to enhance flow, circulation, and/or mixing action of analytes in a fluid sample, thereby enhancing analyte capture on the microarray.

The presently disclosed microfluidic system includes surface-attached structures (e.g., a micropost array) and a microarray (e.g., a nucleic acid microarray, a protein array, an antibody array, a small molecule array, or the like) that are separated by gap, wherein the gap contains liquid, such as, but not limited to, fluid sample. Such a gap may at least partially define a chamber through with the liquid flows. Further, the microfluidic system includes an actuation mechanism for actuating the surface-attached structures (e.g., microposts of a micropost array). For example, microposts are surface-attached posts wherein each micropost includes a proximal end attached to a substrate and a distal end that extends into the gap between the micropost array and the microarray. Accordingly, the distal ends of the microposts extend into the fluid sample that is in the gap between the micropost array and the microarray. The actuation mechanism is used to generate an actuation force in proximity to the micropost array to actuate the microposts, thereby compelling at least some of the microposts to exhibit motion.

In the presently disclosed microfluidic system, the motion of the surface-attached structures (e.g., microposts) due to the actuation force serves to enhance flow, circulation, and/or mixing action of the fluid sample with respect to the full area of the microarray as compared with the use of diffusion alone for flow and/or mixing. Accordingly, an aspect of the presently disclosed microfluidic system and method is that it can be used to significantly reduce the reaction time (i.e., accelerate reactions) compared with microarray applications that rely on diffusion alone for flow and/or mixing. For example, in microarray applications, the presently disclosed microfluidic system can be used to reduce the reaction time from hours or days to a few minutes only. Particularly, the presently disclosed microfluidic system and methods can be used to reduce the reaction time by at least about five times (5×), at least about six times (6×), at least about seven times (7×), at least about eight times (8×), at least about nine times (9×), or at least about ten times (10×), as compared to microfluidic systems and methods that do not utilize the motion of surface-attached structures (e.g., microposts) due to actuation forces to enhance the flow, circulation, and/or mixing action of a fluid sample. This is particularly useful in microarray applications in which the "time to result" is important (e.g., POC devices).

Further, because of the enhanced flow, circulation, and/or mixing action of the fluid sample and accelerated reactions, another aspect of the presently disclosed microfluidic system and method is that in microarray applications in which the analyte concentration is low, such as in liquid biopsy/circulating cell-free DNA tests, it can be used to increase analyte utilization and therefore improve sensitivity of the detection operations as compared with microarray applications that rely on diffusion alone for flow and/or mixing.

Yet another aspect of the presently disclosed microfluidic system and method is that it provides surface-attached structures (e.g., micropost arrays) in combination with a microarray and is therefore able to process multiple target analytes with respect to multiple capture sites in a single reaction chamber.

Yet another aspect of the presently disclosed microfluidic system and method is that it provides enhanced flow, circulation, and/or mixing action of the fluid sample and accelerated reactions via the surface-attached structures (e.g., a micropost array), wherein the surface attached structures are a simple and low cost stirring mechanism compared with microfluidics devices that include, for example, pumping mechanisms to move the fluid.

Still another aspect of the presently disclosed microfluidic system and method is that it includes the surface-attached structures (e.g., a micropost array) in combination with the microarray while maintaining compatibility with common detection methods (e.g., optical and/or electrical detection systems).

In another embodiment, the presently disclosed microfluidic system does not include a microarray separate from the surface-attached structures, and instead includes analyte capture elements on the surface-attached structures themselves (e.g., a micropost array). Namely, the surface-attached structures are functionalized with analyte capture elements. In some embodiments, such a configuration may be characterized as including a microarray that is integrated with or provided by the array of surface-attached structures.

In yet another embodiment, the presently disclosed microfluidic system includes the combination of both the microarray and surface-attached structures (e.g., microposts) that are functionalized with analyte capture elements.

Figure 11:
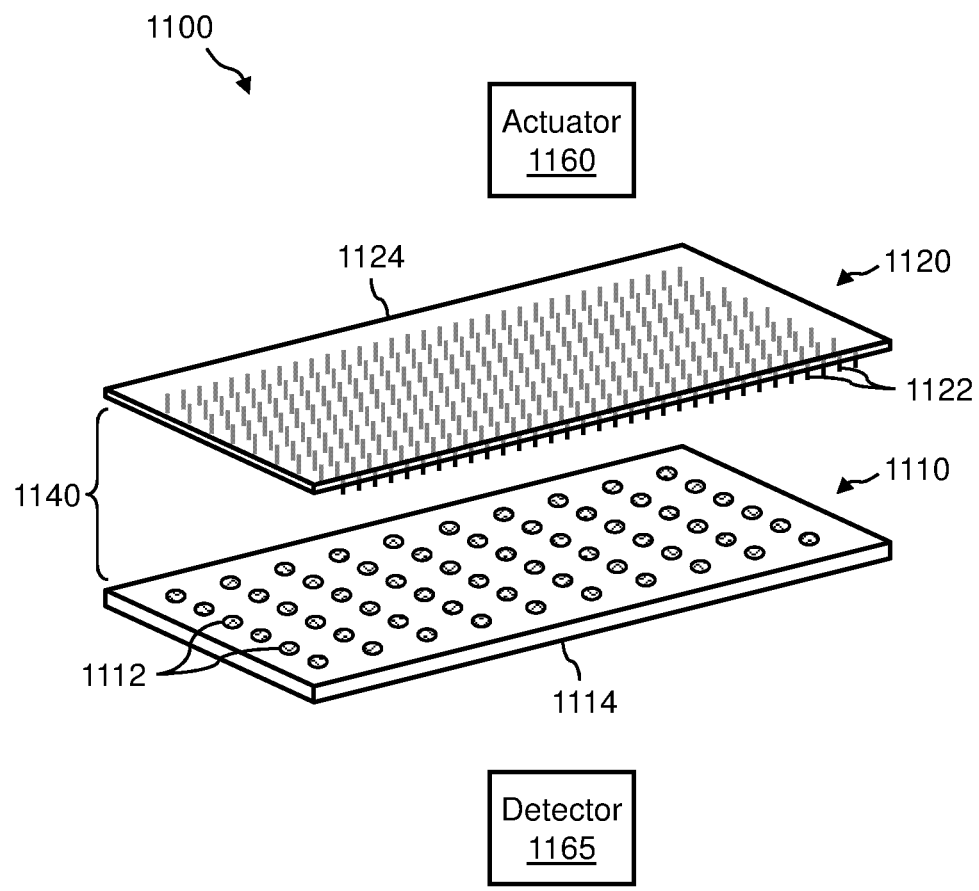
FIG. 11 is a perspective view of an example of a microfluidic system that includes a microarray positioned in relation to a micropost array, according to an embodiment disclosed herein.

FIG. 11 illustrates a perspective view of an example of a microfluidic system 1100 that includes a microarray positioned in relation to a micropost array, wherein the actuated motion of the microposts is used to enhance flow, circulation, and/or mixing action for analyte capture on a microarray. In this example, microfluidic system 1100 includes a microarray 1110 and a micropost array 1120 that are separated by a gap 1140, wherein gap 1140 can contain liquid, such as, but not limited to, fluid sample. Microfluidic system 1100 includes an actuator 1160 in proximity to micropost array 1120. Optionally, microfluidic system 1100 may include a detector 1165 in proximity to microarray 1110 as often microarrays are scanned after runtime in a separate instrument.

Microarray 1110 can be any type of microarray for performing assays. Examples of microarrays include, but are not limited to, DNA microarrays (e.g., cDNA microarrays, oligonucleotide microarrays, bacterial artificial chromosome (BAC) microarrays and single nucleotide polymorphism (SNP) microarrays), model-based meta-analysis of chromatin immunoprecipitation (MM-ChIP) arrays, protein microarrays, peptide microarrays, tissue microarrays, cellular microarrays, small molecule microarrays, chemical compound microarrays, antibody microarrays, carbohydrate arrays, phenotype microarrays, reverse phase protein microarrays, and the like.

Microarray 1110 includes an arrangement (e.g., an array) of capture sites 1112 on a microarray substrate 1114. In one example, the capture sites 1112 are analyte capture elements (or binding agents, or probes), wherein each capture site 1112 or groups of capture sites 1112 can be functionalized to capture different analytes. Microarray substrate 1114 can be, for example, a glass or silicon substrate. In the case of a glass substrate 1114, detector 1165 can be a florescence-based optical detection mechanism. In the case of a silicon substrate 1114 in which microarray 1110 is a semiconductor array, detector 1165 can be an electrical signal-based detection mechanism.

Micropost array 1120 includes an arrangement (e.g., an array) of microposts 1122 on a micropost substrate 1124. Microposts 1122 are surface-attached posts wherein each micropost 1122 includes a proximal end attached to micropost substrate 1124 and a distal end that extends into gap 1140 between microarray 1110 and micropost array 1120. Accordingly, the distal ends of micropost 1122 extend into the fluid sample (not shown) that is in gap 1140 between microarray 1110 and micropost array 1120. In one example, microposts 1122 are chemically inert and will not react with target analytes in the fluid sample. However, in another example, the surfaces of the microposts 1122 can be functionalized with analyte capture elements.

Microposts 1122 in micropost array 1120 are designed to exhibit motion when in the presence of an actuation force. As used herein, the term "actuation force" refers to the force applied to microposts 1122. Actuator 1160 is used to generate an actuation force in proximity to micropost array 1120 that compels at least some of microposts 1122 to exhibit motion. The actuation force may be, for example, magnetic, thermal, sonic, optical, electrical, and/or vibrational. Further, the actuation force may be applied as a function of frequency or amplitude, or as an impulse force (i.e., a step function). Similarly, other actuation forces may be used without departing from the scope of the present invention, such as fluid flow across micropost array 1120.

By actuating microposts 1122 and causing motion thereof, the fluid sample in gap 1140 is in effect stirred or caused to flow or circulate within gap 1140 and across the surface area of microarray 1110. Micropost array 1120 that includes the arrangement of microposts 1122 is based on, for example, the microposts described in the U.S. Pat. No. 9,238,869, entitled "Methods and systems for using actuated surface-attached posts for assessing biofluid rheology," issued on Jan. 19, 2016; the entire disclosure of which is incorporated herein by reference. The '869 patent describes methods, systems, and computer readable media for using actuated surface-attached posts for assessing biofluid rheology. According to one aspect, a method of the '869 patent for testing properties of a biofluid specimen includes placing the specimen onto a micropost array having a plurality of microposts extending outwards from a substrate, wherein each micropost includes a proximal end attached to the substrate and a distal end opposite the proximal end, and generating an actuation force in proximity to the micropost array to actuate the microposts, thereby compelling at least some of the microposts to exhibit motion. The method of the '869 patent further includes measuring the motion of at least one of the microposts in response to the actuation force and determining a property of the specimen based on the measured motion of the at least one micropost.

In one example, according to the '869 patent, microposts 1122 and substrate 1124 of micropost array 1120 can be formed of polydimethylsiloxane (PDMS). Further, microposts 1122 may include a flexible body and a metallic component disposed on or in the body, wherein application of a magnetic or electric field actuates microposts 1122 into movement relative to the surface to which they are attached. In this example, the actuation force generated by actuator 1160 is a magnetic and/or electrical actuation force. More details of micropost array 1120 and microposts 1122 are shown and described hereinbelow with reference to FIG. 12A through FIG. 15B.

Figure 12A:
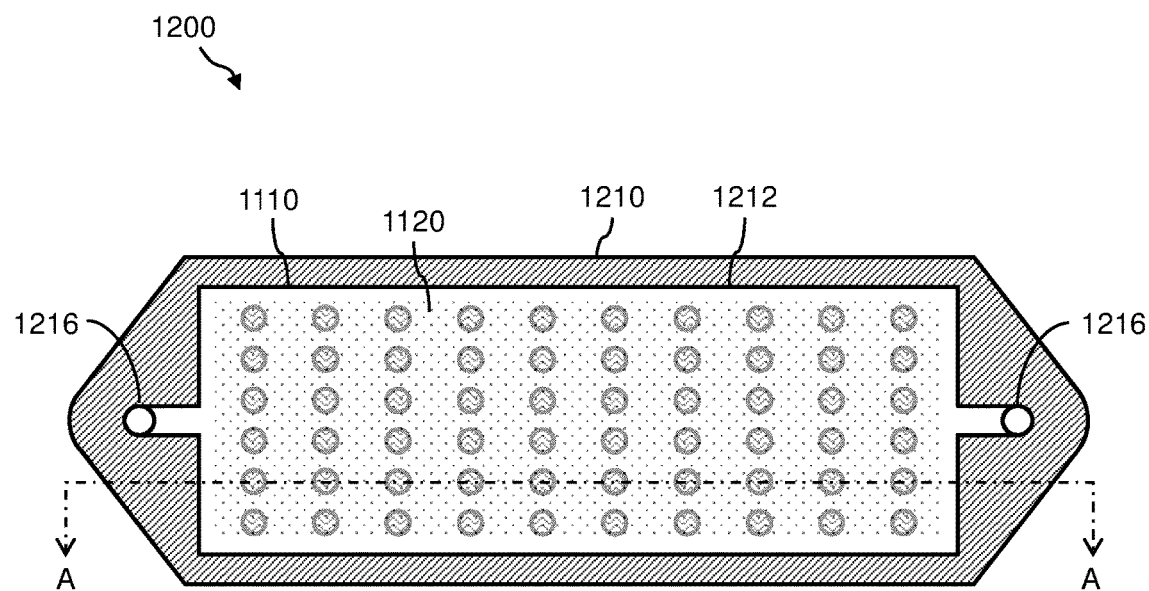
FIG. 12A and FIG. 12B are a plan view and a cross-sectional view, respectively, of an example of a flow cell that is based on the microfluidic system of FIG. 11, according to an embodiment disclosed herein.
Figure 12B:
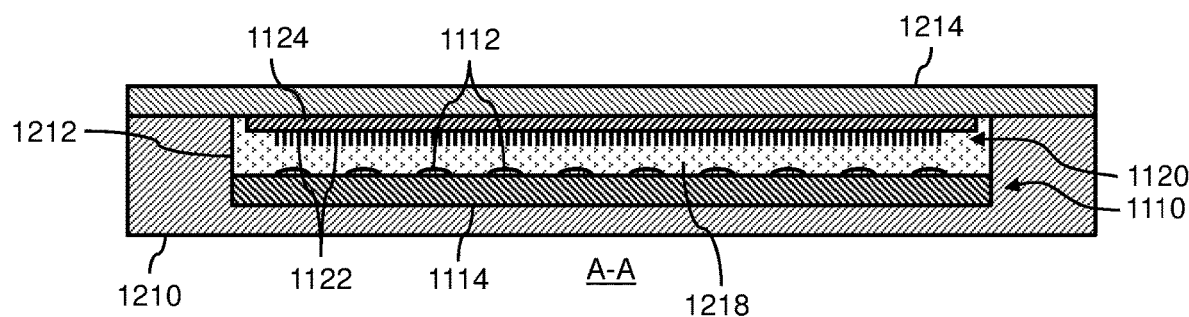

FIG. 12A and FIG. 12B illustrate a plan view and a cross-sectional view, respectively, of an example of a flow cell 1200 that is based on microfluidic system 1100 of FIG. 1 that includes microarray 1110 positioned in relation to micropost array 1120. Namely, FIG. 12B is a cross-sectional view taken along line A-A of FIG. 12A.

In this example, flow cell 1200 includes a first substrate 1210 that includes a reaction chamber 1212 integrated therein, wherein reaction chamber 1212 is a space or void in substrate 1210. Substrate 1210 is capped with a second substrate 1214, wherein substrate 1214 encloses reaction chamber 1212. Substrate 1210 and substrate 1214 can be formed, for example, of glass or plastic. In one example, flow cell 1200 includes two loading ports 1216 (e.g., one at each end) for supplying liquid (e.g., fluid sample 1218 that includes target analytes) into or out of reaction chamber 1212.

Reaction chamber 1212 is sized to receive microarray 1110 such that the capture sites 1112 face into reaction chamber 1212. A microarray, such as microarray 1110, can support, for example, from a few dozen capture sites up to many thousands of capture sites. The size of reaction chamber 1212 can vary according to the size of microarray 1110. For example, reaction chamber 1212 can hold from about 1 microliters to about 500 microliters of fluid sample 1218. Reaction chambers can come in all shapes and sizes. A typical reaction chamber size might be, for example, about 1 mm×1 mm. In one example, both substrate 1124 of micropost array 1120 and substrate 1114 of microarray 1110 are 1-inch×3-inch glass slides, wherein the entirety of the 1-inch×3-inch substrate 1124 is covered with microposts 1122 and the 1-inch×3-inch substrate 1114 has three 10 mm×10 mm microarrays on it.

Additionally, micropost array 1120 is mounted on substrate 1214 such that microposts 1122 are facing into reaction chamber 1212. Namely, substrate 1124 of micropost array 1120 is mounted on the inside surface of substrate 1214 and microposts 1122 are facing capture sites 1112 of microarray 1110. The length of microposts 1122 can vary. The length of microposts 1122 can be from about 1 μm to about 100 μm in one example, or can be from about 10 μm to about 50 μm in another example. Further, the space between the distal ends of microposts 1122 and microarray 1110 can vary. The space between the distal ends of microposts 1122 and microarray 1110 can be from about 0 μm to about 50 μm in one example, or can be from about 1 μm to about 30 μm in another example. In another example, the space between the distal ends of microposts 1122 and microarray 1110 can be about equal to the length of microposts 1122. In yet another example, the space between the distal ends of microposts 1122 and microarray 1110 can be about 10 μm or more or less than 10 m.

Figure 13A:
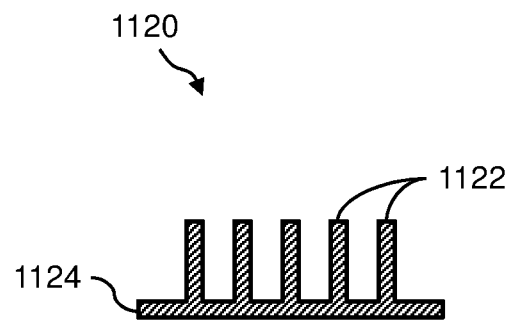
FIG. 13A and FIG. 13B are side views of examples of microposts according to an embodiments disclosed herein.
Figure 13B:
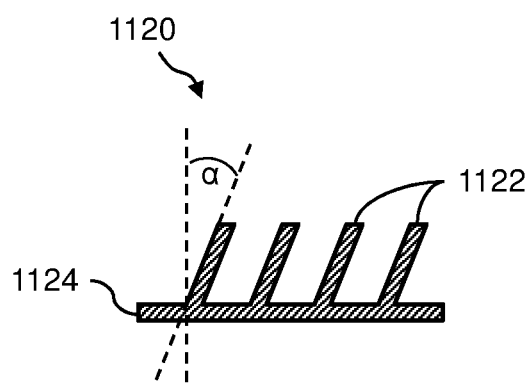

FIG. 13A and FIG. 13B illustrate side views of an example of microposts 1122. Again, microposts 1122 and substrate 1124 of micropost array 1120 can be formed, for example, of PDMS. The length, diameter, geometry, orientation, and pitch of microposts 1122 in micropost array 1120 can vary. For example, the length of microposts 1122 can vary from about 1 μm to about 100 μm. The diameter of microposts 1122 can vary from about 0.1 μm to about 10 μm. The cross-sectional shape of microposts 1122 can vary. For example, the cross-sectional shape of microposts 1122 can circular, ovular, square, rectangular, triangular, and so on. The orientation of microposts 1122 can vary. For example, FIG. 13A shows microposts 1122 oriented substantially normal to the plane of substrate 1124, while FIG. 3B shows microposts 1122 oriented at an angle α with respect to normal of the plane of substrate 1124. In a neutral position with no deflection force applied, the angle α can be, for example, from about 0 degrees to about 45 degrees.

Figure 14A:
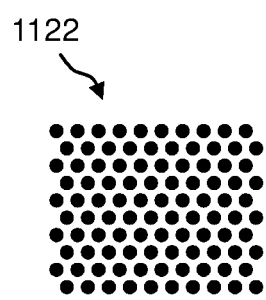
FIG. 14A through FIG. 14E are plan views of examples of configurations of the micropost array according to an embodiments disclosed herein.
Figure 14B:
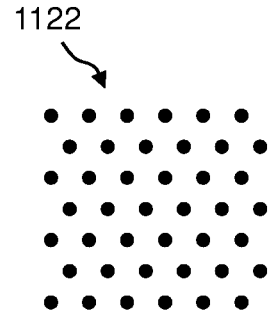
Figure 14C:
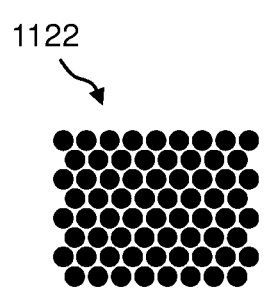
Figure 14D:
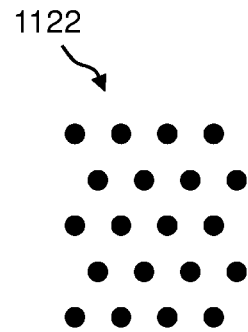
Figure 14E:
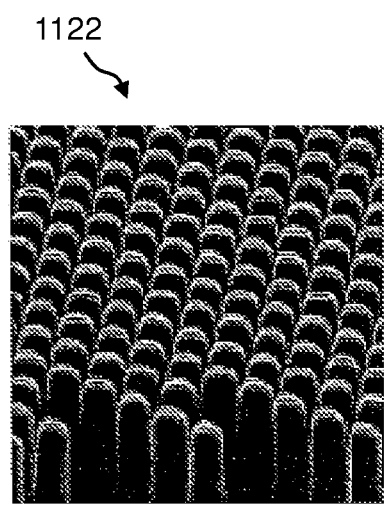

Further, the pitch of microposts 1122 within micropost array 1120 can vary, for example, from about 0 μm to about 50 μm. For example, FIG. 14A through FIG. 14D illustrate plan views of examples of various configurations of micropost array 1120. Namely, FIG. 14A shows an example of microposts 1122 that are 0.6 μm in diameter and spaced 1.4 μm apart. FIG. 14B shows an example of microposts 1122 that are 0.6 μm in diameter and spaced 2.6 μm apart. FIG. 14C shows an example of microposts 1122 that are 1 μm in diameter and spaced 1.5 μm apart. FIG. 14D shows an example of microposts 1122 that are 1 μm in diameter and spaced 3 μm apart. It is understood that the size and dimensions depicted in FIG. 14A through FIG. 14D are exemplary only and not limiting. FIG. 14E shows a scanning electron microscope (SEM) image of an example of a micropost array 1120. Further, FIG. 14A through FIG. 14E show the rows of microposts 1122 staggered or offset, which is exemplary only. In another configuration, the density of the microposts 1122 is lower than the density of the capture sites 1112 of microarray 1110.

Figure 15A:
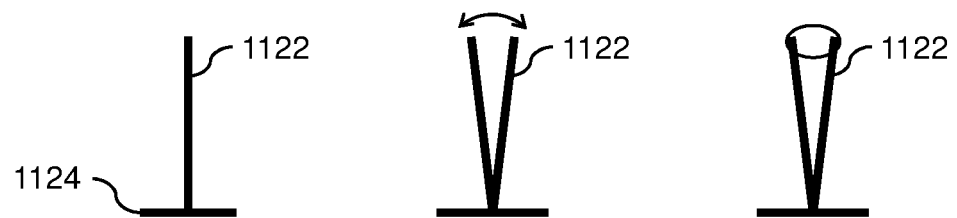
FIG. 15A and FIG. 15B are side views of a micropost and show examples of actuation motion thereof.
Figure 15B:
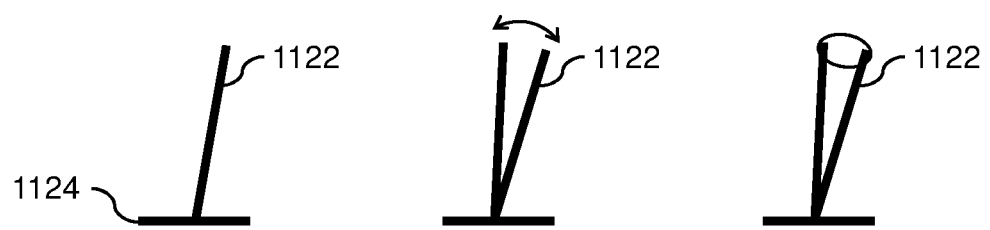

FIG. 15A and FIG. 15B illustrate side views of a micropost 1122 and show examples of actuation motion thereof. Namely, FIG. 15A shows an example of a micropost 1122 oriented substantially normal to the plane of substrate 1124. FIG. 15A shows that the distal end of the micropost 1122 can move (1) with side-to-side two-dimensional motion only with respect to the fixed proximal end or (2) with circular motion with respect to the fixed proximal end, which is a cone-shaped motion. By contrast, FIG. 15B shows an example of a micropost 1122 oriented at an angle with respect to the plane of substrate 1124. FIG. 15B shows that the distal end of the micropost 1122 can move (1) with tilted side-to-side two-dimensional motion only with respect to the fixed proximal end or (2) with tilted circular motion with respect to the fixed proximal end, which is a tilted cone-shaped motion.

Figure 16:
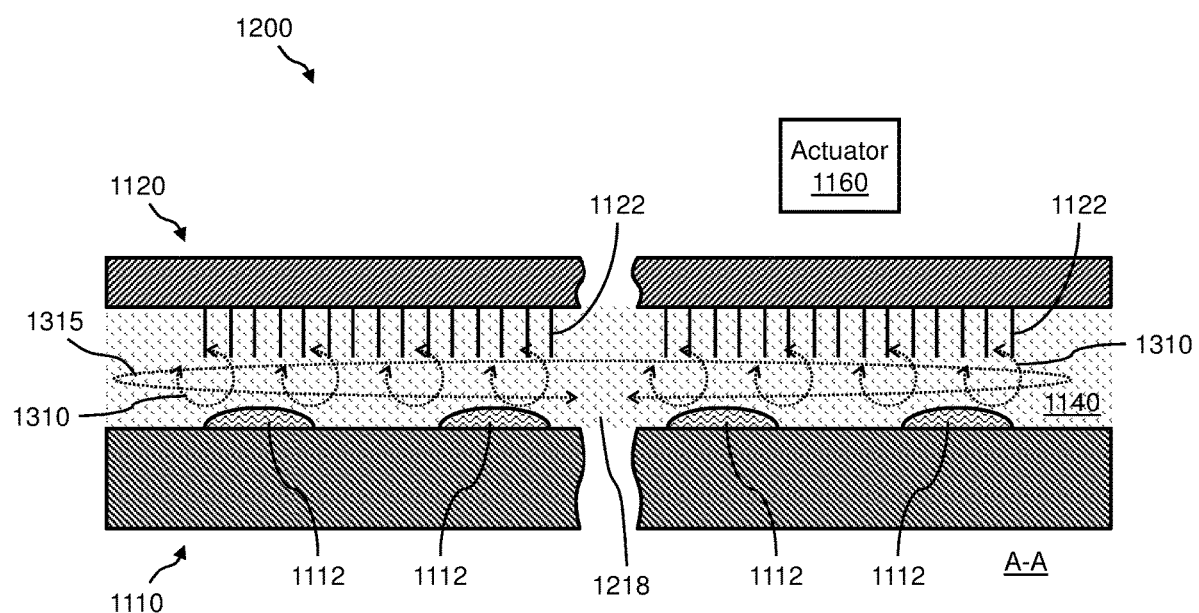
FIG. 16 shows a close up cross-sectional view of a portion of an example of a reaction chamber of the flow cell shown in FIG. 12A and FIG. 12B and show the operation thereof, according to an embodiment disclosed herein.

FIG. 16 shows a close up cross-sectional view of a portion of reaction chamber 1212 of flow cell 1200 shown in FIG. 12A and FIG. 12B and shows the operation thereof. Again, the length of microposts 1122 can vary, for example, from about 1 µm to about 100 µm. Again, the space between the distal ends of microposts 1122 and microarray 1110 can vary, for example, from about 0 µm to about 50 µm. In another example, the space between the distal ends of microposts 1122 and microarray 1110 can be about equal to the length of microposts 1122. In yet another example, the space between the distal ends of microposts 1122 and microarray 1110 can be about 10 µm or more or less than 10 µm.

In operation, actuator 1160 generates an actuation force in proximity to micropost array 1120 that compels at least some of microposts 1122 to exhibit motion. In so doing, both regions of local circulation 1310 and bulk circulation 1315 occurs within reaction chamber 1212 of flow cell 1200. In the presence of regions of local circulation 1310 and bulk circulation 1315, target analytes in fluid sample 1218 can be rapidly flowed through the bulk fluid sample 1218 to its corresponding capture site 1112 on microarray 1110. Namely, due to the presence of regions of local circulation 1310 and bulk circulation 1315 created by the motion of microposts 1122, in reaction chamber 1212 of flow cell 1200 the reaction time can be significantly reduced (i.e., accelerated reactions) compared with microarray applications that rely on diffusion alone for flow and/or mixing. That is, any given target analyte can be rapidly flowed through the bulk fluid sample 1218 and to its corresponding capture site 1112 (i.e., its corresponding analyte capture element). For example, compared with microarray applications that rely on diffusion alone, flow cell 1200, which is based on microfluidic system 1100 of FIG. 11, can be used to reduce the reaction time from hours or days to a few minutes only.

Microfluidic system 1100 and/or flow cell 1200 are not limited to the configurations shown in FIG. 11 through FIG. 16. Other configurations of microfluidic system 1100 and/or flow cell 1200 are possible, examples of which are shown and described hereinbelow with reference to FIG. 17A, FIG. 17B, FIG. 18A, and FIG. 18B.

Figure 17A:
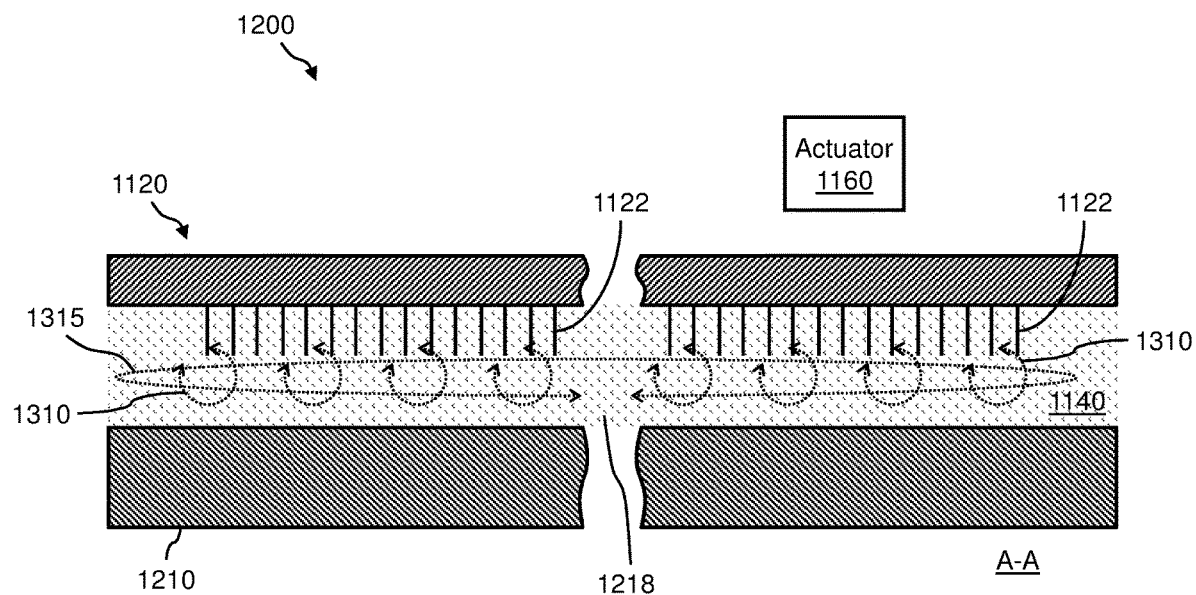
FIG. 17A and FIG. 17B show an example of the flow cell shown in FIG. 12A and FIG. 12B that includes analyte capture elements on the microposts according to an embodiment disclosed herein.
Figure 17B:
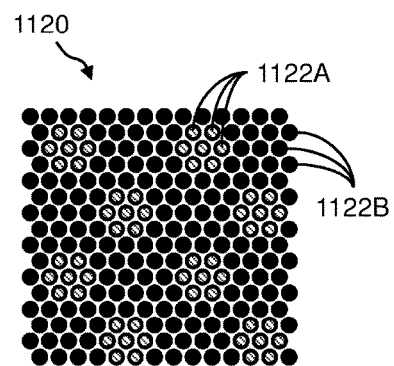

FIG. 17A and FIG. 17B show an example of flow cell 1200 shown in FIG. 12A and FIG. 12B that does not include the microarray 1110 and instead includes analyte capture elements on the microposts 1122 themselves. Namely, individual or groups of microposts 1122 within micropost array 1120 are functionalized with analyte capture elements. In some embodiments, microposts 1122 of micropost array 1120 may include one or more capture elements (binding agents) exhibiting a specificity for one or more target analytes in a fluid sample. In one example, microposts 1122 can be functionalized by integration of the binding moiety into the bulk elastomer. For example, this can be an elastomer made of monomers that have functional groups as part of the chain, an elastomer made of multiple different monomers that link together with one (or more) containing a binding moiety (block co-polymer, for example), or an elastomer doped with a functionalizing agent that is not cross-linked into the matrix. In another example, microposts 1122 can be functionalized by surface-functionalization. Namely, the binding moiety is attached to (e.g., grafted, bonded, etc.) or sits atop the surface of the micropost 1122. This treatment can be performed on micropost array 1120 after it is made or can be added to the mold so that it is integrated into the surface upon curing.

Referring now to FIG. 17B, micropost array 1120 can include certain microposts 1122 that have been functionalized with capture elements (binding agents) exhibiting a specificity for one or more target analytes in fluid sample 1218, hereafter called functionalized microposts 1122A. Micropost array 1120 can also include certain microposts 1122 that have not been functionalized (i.e., are chemically inert), hereafter called inert microposts 1122B. In effect, groups of functionalized microposts 1122A, which are arranged among inert (or non-functionalized, or passive) microposts 1122B, create capture sites that substantially mimic capture sites 1112 of microarray 1110. The configuration shown in FIG. 17A and FIG. 17B is not limited to groups of functionalized microposts 1122A. In another example, groups and/or individual functionalized microposts 1122A can be arranged among inert microposts 1122B.

Figure 18A:
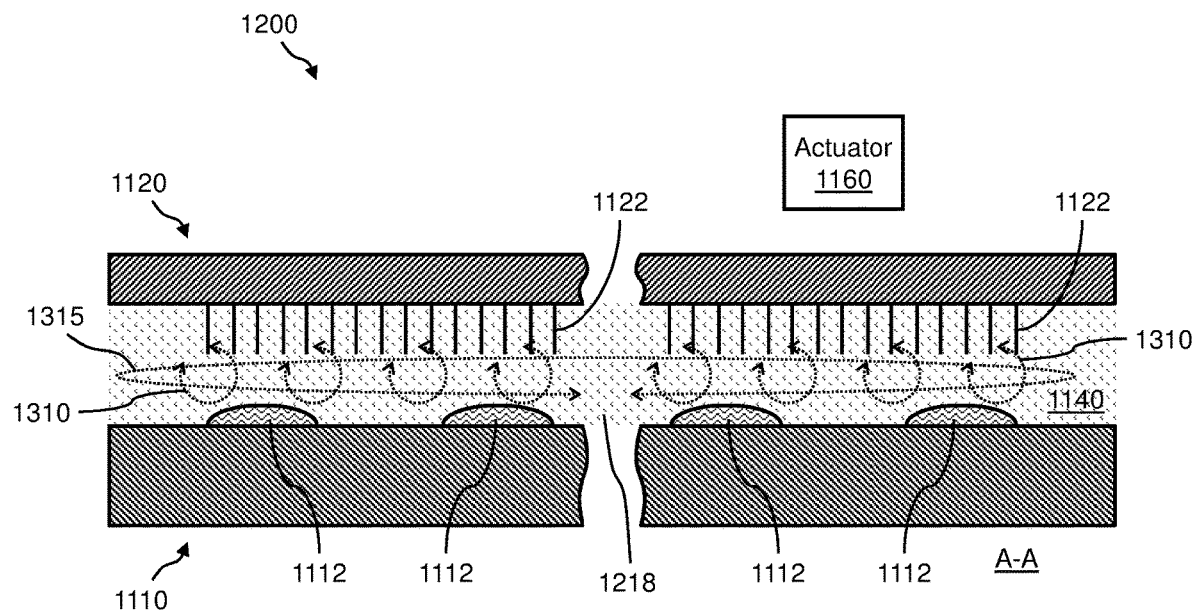
FIG. 18A and FIG. 18B show an example of the flow cell shown in FIG. 12A and FIG. 12B that includes a microarray in combination with analyte capture elements on the microposts according to an embodiment disclosed herein.
Figure 18B:
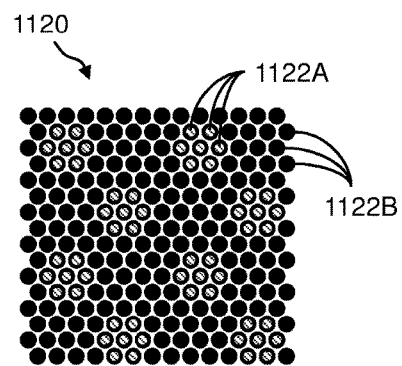

In another embodiment, FIG. 18A and FIG. 18B show an example of flow cell 1200 shown in FIG. 12A and FIG. 12B that includes the combination of both microarray 1110 that includes capture sites 1112 and microposts 1122 that are functionalized with analyte capture elements. In effect, individual and/or groups of functionalized microposts 1122A create capture sites arranged opposite capture sites 1112 of microarray 1110. In this configuration, a double array of capture elements is formed, one facing the other.

Figure 19:
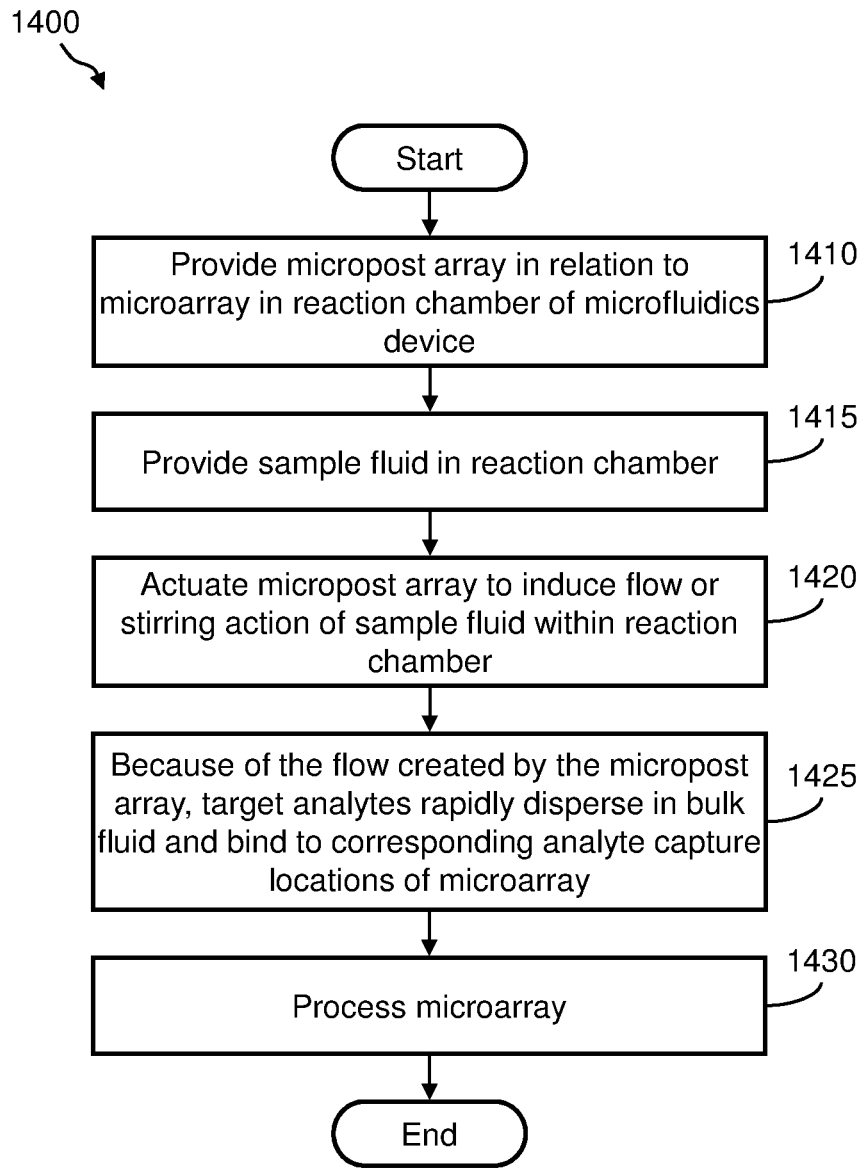
FIG. 19 is a flow diagram of an example of a method of using a micropost array in conjunction with a microarray for rapidly flowing target analytes through the bulk fluid.

FIG. 19 illustrates a flow diagram of an example of a method 1400 of using a micropost array (e.g., micropost array 1120) in combination with a microarray (e.g., microarray 1110) for rapidly flowing target analytes through a bulk fluid. Method 1400 may include, but is not limited to, the following steps.

At a step 1410, a micropost array is provided that is positioned in relation to a microarray in the reaction chamber of microfluidics device. For example, flow cell 1200 of FIG. 12, which is based on microfluidic system 1100 of FIG. 11, provides a micropost array 1120 positioned in relation to microarray 1110 within reaction chamber 1212 and with a space between micropost array 1120 and microarray 1110.

At a step 1415, fluid sample is provided within the reaction chamber. For example, in flow cell 1200, a bulk amount of fluid sample 1218 is loaded into reaction chamber 1212 and in the space between micropost array 1120 and microarray 1110.

At a step 1420, the micropost array is actuated to induce flow or stirring action of the fluid sample within the reaction chamber. For example, in flow cell 1200, micropost array 1120 is actuated using actuator 1160 to induce flow or stirring action in fluid sample 1218 within reaction chamber 1212. Namely, actuator 1160 is used to generate an actuation force in proximity to micropost array 1120 to actuate microposts 1122, thereby compelling at least some of microposts 1122 to exhibit motion. Because the distal ends of microposts 1122 extend into the bulk fluid sample 1218, the motion thereof creates a flow or stirring action of fluid sample 1218 within reaction chamber 1212.

At a step 1425, because of the flow created by the micropost array, the target analytes rapidly disperse in the bulk fluid and bind to their corresponding analyte capture locations of the microarray. For example, in flow cell 1200, because of the flow created by micropost array 1120, the target analytes rapidly disperse in the bulk fluid sample 1218 and bind to their corresponding analyte capture locations (i.e., capture sites 1112) of microarray 1110. Namely, target analytes rapidly disperse due to the presence of regions of local circulation 1610 and bulk circulation 1615 created by the motion of microposts 1122, in reaction chamber 1212 of flow cell 1200.

At a step 1430, after a certain amount of time, the microarray is processed. For example, in flow cell 1200, after a certain amount of time, microarray 1110 is processed. Namely, detector 1165 can be used to analyze the absence and/or presence of certain target analytes captured by microarray 1110.

FIG. 19 is also representative of a microfluidic system or flow cell configured to carry out the method just described.

In summary and referring again to FIG. 11 through FIG. 19, using the presently disclosed microfluidic system 1100, flow cell 1200, and/or method 1400, the reaction time can be significantly reduced (i.e., accelerated reactions) compared with microarray applications that rely on diffusion alone for flow and/or mixing. For example, compared with microarray applications that rely on diffusion alone, microfluidic system 1100, flow cell 1200, and/or method 1400 can be used to reduce the reaction time from hours or days to a few minutes only. This is particularly useful in microarray applications in which the "time to result" is important (e.g., POC devices).

Further, because of the enhanced flow, circulation, and/or mixing action of the fluid sample and accelerated reactions, in microarray applications in which the analyte concentration is low, such as liquid biopsy/circulating cell-free DNA tests, microfluidic system 1100, flow cell 1200, and/or method 1400 can be used to increase analyte utilization and therefore improve sensitivity of the detection operations as compared with microarray applications that rely on diffusion alone for flow and/or mixing.

Further, microfluidic system 1100, flow cell 1200, and/or method 1400 provide a micropost array (e.g., micropost array 1120) in combination with a microarray (e.g., microarray 1110) and is therefore able to process multiple target analytes with respect to multiple capture locations in a single reaction chamber.

Further, microfluidic system 1100, flow cell 1200, and/or method 1400 provide enhanced flow, circulation, and/or mixing action of the fluid sample and accelerated reactions via micropost array 1120, wherein micropost array 1120 is a simple and low cost stirring mechanism compared with, for example, microfluidics devices that include pumping mechanisms.

Further, microfluidic system 1100, flow cell 1200, and/or method 1400 provide a micropost array (e.g., micropost array 1120) in combination with a microarray (e.g., microarray 1110) while maintaining compatibility with current detection methods (e.g., optical and/or electrical detection systems).

Figure 20A:
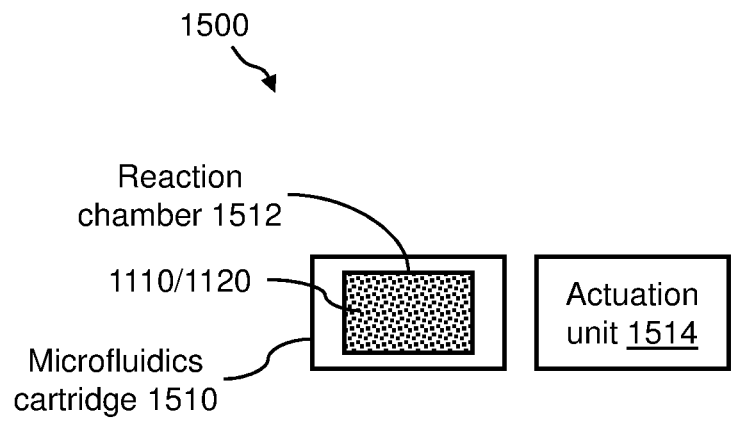
FIG. 20A and FIG. 20B are block diagrams of examples of standalone microfluidic systems that can include a micropost array and a microarray.

The presently disclosed micropost array (e.g., micropost array 1120) positioned in relation to a microarray (e.g., microarray 1110), wherein the actuated motion of microposts (e.g., microposts 1122) is used to enhance flow, circulation, and/or mixing action for analyte capture on a microarray, as described herein above with reference to FIG. 11 through FIG. 19, can be used in a standalone device, such as, but not limited to, any microfluidics device (e.g., a disposable microfluidics cartridge, a digital microfluidics cartridge, a flow cell, a droplet actuator, or the like). In one example, FIG. 20A shows a block diagram of an example of a microfluidic system 1500 that includes a microfluidics cartridge 1510 (e.g., a portable microfluidics cartridge), wherein microfluidics cartridge 1510 can be based on, for example, microfluidic system 1100 and/or flow cell 1200 described herein above with reference to FIG. 11 through FIG. 19. Microfluidic system 1500 also includes an actuation unit 1514, wherein actuation unit 1514 may be in close proximity to microfluidics cartridge 1510.

Microfluidics cartridge 1510 includes a reaction chamber 1512. Processing and/or analysis of a fluid sample may be performed within reaction chamber 1512. A micropost array (e.g., micropost array 1120) and a microarray (e.g., microarray 1110) may be provided inside reaction chamber 1512, wherein the micropost array 1120 may be used to affect the processing and/or analysis of a fluid sample within reaction chamber 1512. In one example, the microposts may include a flexible body and a metallic component disposed on or in the body, wherein application of a magnetic or electric field actuates the microposts into movement relative to the surface to which they are attached. In some embodiments, the microposts may include one or more capture elements (binding agents) exhibiting a specificity for one or more target analytes in a fluid sample.

As used herein, the term "actuation force" refers to the force applied to the microposts. Actuation unit 1514 is used to generate an actuation force in proximity to the micropost array that compels at least some of the microposts to exhibit motion. The actuation force may be, for example, magnetic, thermal, sonic, optical, electrical, and/or vibrational. Further, the actuation force may be applied as a function of frequency or amplitude, or as an impulse force (i.e., a step function). Similarly, other actuation forces may be used without departing from the scope of the present invention, such as fluid flow across the micropost array.

Figure 20B:
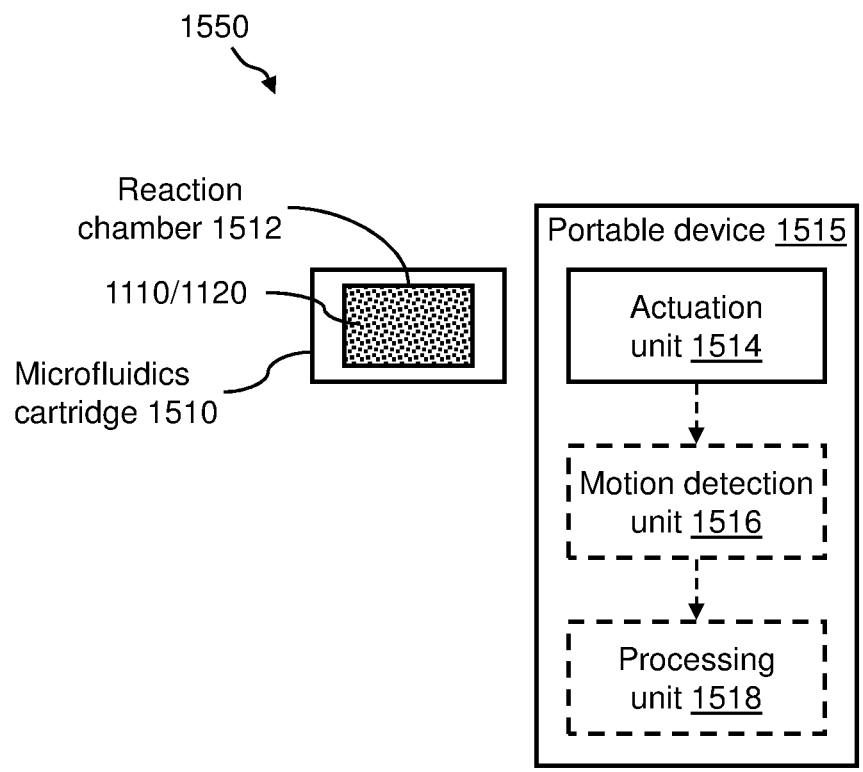

In another example, FIG. 20B shows a block diagram of an example of a microfluidic system 1550 that includes microfluidics cartridge 1510 that is described in FIG. 20A and a portable device 1515. Portable device 1515 includes actuation unit 1514 that is described in FIG. 20A. Optionally, portable device 1515 includes a motion detection unit 1516 and a processing unit (or controller) 1518.

Optionally, as the microposts exhibit motion in response to the actuation force from actuation unit 1514, the motion of the microposts may be measured or detected using motion detection unit 1516. Motion detection unit 1516 may be configured to measure the motion of individual or specific microposts, groups of microposts, or all the microposts. In motion detection unit 1516, the means for detecting and measuring this micropost behavior may include, for example, an optical (e.g., an imaging system), magnetic (e.g., a magnetic pickup coil), sonic, and/or electrical tracking system.

Optionally, measurement data from motion detection unit 1516 is provided to processing unit 1518 for calculations and analysis. In another example, processing unit 1518 can be physically separate from portable device 1515, wherein processing unit 1518 may be in communication with portable device 1515 via any wired or wireless means. Measurement data from motion detection unit 1516 can be any information about the motion of the microposts. Processing unit 1518 processes the measurement data in order to determine at least one property of the specimen based on the measured motion of the microposts. The calculations and analysis performed by processing unit 1518 may include determining a measure of fluid rheology based on the force applied by actuation unit 1514 and the resulting motion detected by motion detection unit 1516. In one example, as a blood specimen begins to clot, the motion of the microposts becomes restricted, and the resulting measurements may be used to indicate and determine clotting time.

Figure 21:
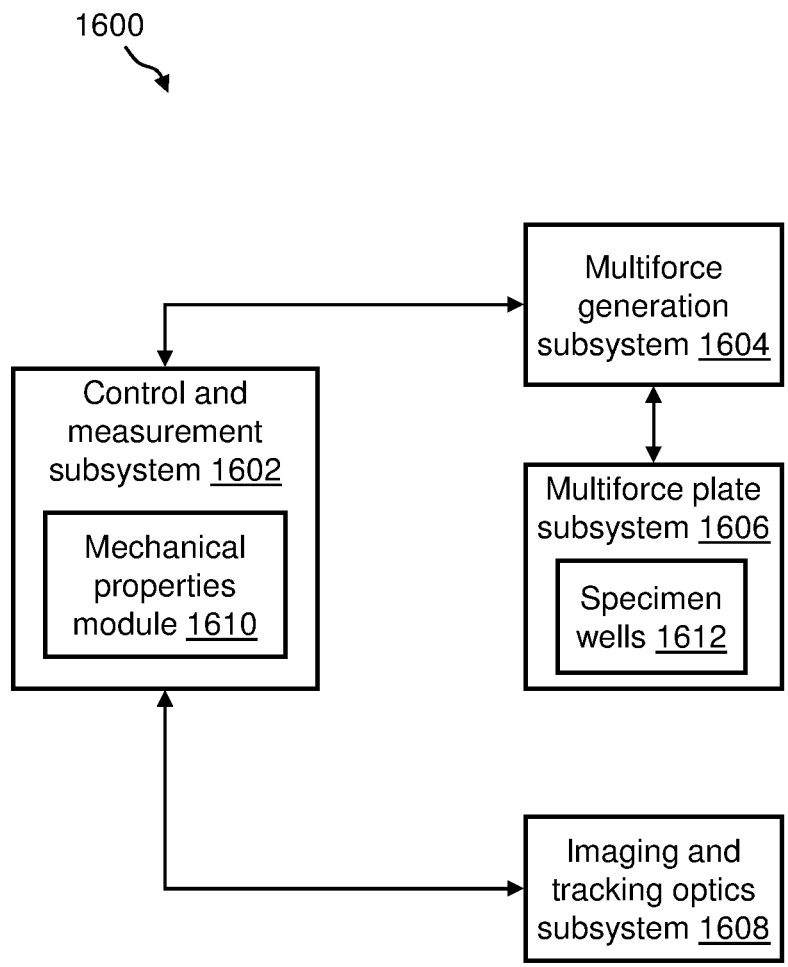
FIG. 21 is a block diagram of an example of a high-throughput screening system that can include a micropost array and a microarray.

The presently disclosed micropost array (e.g., micropost array 1120) positioned in relation to a microarray (e.g., microarray 1110), wherein the actuated motion of microposts (e.g., microposts 1122) is used to enhance flow, circulation, and/or mixing action for analyte capture on a microarray, as described herein above with reference to FIG. 11 through FIG. 19 can be used in a high-throughput system. For example, FIG. 21 shows a block diagram of an example of a high-throughput screening system 1600 that includes mechanisms for receiving and processing microarrays based on configurations shown and described with reference to microfluidic system 1100 and/or flow cell 1200 of FIG. 11 through FIG. 19.

In one implementation of high-throughput screening system 1600, the actuation and optical system may be similar to that described in International Patent Pub. No. WO/2008/103430, entitled "Methods and systems for multiforce high throughput screening," published on Oct. 9, 2008, the disclosure of which is incorporated herein by reference. High-throughput screening system 1600 is capable of applying a force and measuring micropost responses. In one example, high-throughput screening system 1600 includes a control and measurement subsystem 1602, a multiforce generation subsystem 1604, a multiforce plate subsystem 1606, and an imaging and tracking optical subsystem 1608.

Control and measurement subsystem 1602 may be similar in operation to processing unit 1518 described above in microfluidic system 1550 of FIG. 20B. Control and measurement subsystem 1602 may also include a mechanical properties module 1610 that is used to measure the mechanical properties of the specimen depending on the measured movement of the microposts.

Multiforce generation subsystem 1604 is the actuation portion of high-throughput screening system 1600. Multiforce generation subsystem 1604 may be similar in operation to actuation unit 1514 described above in microfluidic system 1500 of FIG. 20A. In one example, multiforce generation subsystem 1604 comprises a magnetic drive block, such as exciter assembly. Multiforce generation subsystem 1604 may also include an appropriate cooling mechanism (not shown) to dissipate excess heat or to maintain high-throughput screening system 1600 at a target temperature. In one example, multiforce generation subsystem 1604 is capable of producing forces of significant magnitude (e.g., forces greater than 10 nanoNewtons), in multiple directions over a three dimensional sphere, and can be varied at frequencies up to more than three kilohertz.

Multiforce plate subsystem 1606 of high-throughput screening system 1600 may comprise a microtiter well plate that includes a plurality of specimen wells 1612. One or more of the specimen wells 1612 may be configured to include the presently disclosed micropost array (e.g., micropost array 1120) positioned in relation to a microarray (e.g., microarray 1110), wherein the actuated motion of the microposts (e.g., microposts 1122) is used to enhance flow, circulation, and/or mixing action for analyte capture on a microarray, as described herein above with reference to FIG. 11 through FIG. 19. The microtiter well plate may also be coupled with a cover glass sheet that serves as the bottom of the well plate. Multiforce plate subsystem 1606 may also include a plurality of field-forming poles that are used to form a magnetic (or electric) coupling with excitation poles of multiforce generation subsystem 1604.

Imaging and tracking optical subsystem 1608 is the motion detection of high-throughput screening system 1600. Imaging and tracking optical subsystem 1608 may be similar in operation to motion detection unit 1516 described above in microfluidic system 1550 of FIG. 20B. However, one physical difference between an actuation system for a high-throughput screening system and a point of care system is that the actuation system (e.g., multiforce generation subsystem 1604) may be replicated for each well or small group of adjacent wells in a multiwell microtiter plate. The motion detection system for a multiwell microtiter plate may include, but is not limited to, an optical system (e.g., imaging and tracking optical subsystem 1608) that measures scattered light to detect movement of the microposts, an imaging system including a camera that images each well or group of wells in the microtiter plate, or a pick up coil that measures amplitude and phase of a current produced by motion the microposts in each well.

Imaging and tracking optical subsystem 1608 may also be employed to perform several kinds of measurements, either simultaneously with the application of force or after the force sequence has been applied. For example, imaging and tracking optical subsystem 1608 may include a single specimen imaging system with a robotic stage that can systematically position each specimen well of multiforce plate subsystem 1606 over a microscope objective. In another example, imaging and tracking optical subsystem 1608 may include an array based system that is capable of imaging several specimen wells simultaneously. The recorded images may be used to track the micropost position or the like.

EXAMPLES

A few non-limiting Examples of operating a flow cell as described herein to capture targets will now be described. The Examples relate to rare analyte extraction from large volumes of whole blood that, conventionally, has proven to be extremely challenging. These Examples have been included to provide guidance to one of ordinary skill in the art for practicing representative embodiments of the presently disclosed subject matter. In light of the present disclosure and the general level of skill in the art, those of skill can appreciate that the following Examples are intended to be exemplary only and that numerous changes, modifications, and alterations can be employed without departing from the scope of the presently disclosed subject matter.

The prevailing protocols are often modifications of assays designed for much smaller volumes. The workflows tend to be operator-intensive, typically involving centrifugation to concentrate cells into volumes compatible with the available instruments. Known techniques include the use of steric filters, magnetic beads, and columns of packed beads that selectively bind to an analyte. The packing in a column achieves an extremely high surface-area-to-volume ratio, but its small interstices are prone to clogging. A clear-bore column that selectively binds to the analyte would avoid clogging, but the binding efficiency of such systems is prohibitively low because analyte transport to the walls is diffusion limited. Pre-fractionating the sample with conventional techniques (centrifugation, pipetting, etc.) would also minimize clogging, but this involves complex workflows and either highly skilled operators or specialized robotic facilities. Techniques that use magnetic beads can be automated, but their capture efficiency is typically inferior because it is impractical and expensive to achieve the same surface area-to-volume ratio present in the column systems. Also, careful balancing of the bead population to the target cell population is required. Large volumes of the bead reagents are also required, because the bead population must be tuned to the total number of cells, not the number of target cells. Yet, the target cell population may be a tiny fraction (e.g., less than 1%) of the total cell population. As a result, the cost of these assays is very high typically hundreds of dollars per unit of blood. Moreover, the kits associated with known techniques require extensive manual handling.

A flow cell as described herein may overcome these issues. In the Examples described below, the flow cell includes an array of surface-attached structures functionalized with binding agents as described herein.

Example 1—Progenitor Cell Isolation from Whole Blood

In treating bone marrow diseases such as leukemia and multiple myeloma, blood progenitor cells (BPCs) are routinely collected from peripheral blood for transfusion. However, typical clinical practice calls for collection of the full range of monocytes and performs no subsequent purification. The clinical value of enriched or purified transplantation is an active area of research. At a minimum, however, there are dramatic practical concerns about this approach. Protocols often involve freezing and storing liters of extracted cell product from the donor, especially for autologous transfusion. Storing this volume of blood product is expensive and space-intensive. The cell freezing process requires dimethyl sulfoxide (DMSO), a toxic solvent that triggers unpleasant side effects in the patient when the transfusion is administered. A more judicious selection of the cells to be used in transfusion could minimize the volume to be stored and transfused by a factor of 20 or more.

More broadly, curation of the monocyte product extracted during apheresis is an active area of clinical research. This may involve depletion (for example, of t-cells) or enrichment (for example, of CD34 progenitor cells).

The primary method used to select subpopulations of cells is a pull-down assay with magnetic beads. In recent years, new automated systems have improved the throughput of these assays. However, they are still expensive and limited in the volumes that they can process. By contrast, the ideal extraction method would be: 1) scalable and inline, meaning very large volumes (e.g., greater than 1 L) of whole blood or monocyte-enriched product could be processed through a single flow cell; 2) compact and modular, meaning the extraction system could be integrated into other systems (for example, placed in-line with an apheresis system), and that multiple isolation selection steps could be performed simultaneously by placing additional modules in series; and 3) rapid, meaning a cartridge could perform isolation on blood moving as fast (or faster) than the flow rate in a typical apheresis system. Such a system would dramatically streamline clinical research studying targeted transplantation techniques. It could dramatically reduce the storage volumes required for transplantation and the DMSO exposure of patients. If included as a modular component in apheresis systems, it could open the door to a new category of blood product donation, enabling systematic and pervasive BPC banking.

A flow cell as described herein may overcome these issues. Specifically, the surface-attached structures of the flow cell may include a binding agent exhibiting a specific affinity to CD34 progenitor cells. The flow cell may thus be effective for capturing CD34 progenitor cells from a large volume of undiluted whole blood. If needed, the surface-attached structures may be moved under the influence of a magnetic or electric field as described herein to prevent or disrupt clogging. Moreover, because the surface-attached structures are fixed to an underlying substrate, they do not aggregate in the presence of a magnetic field, in contrast to magnetic beads typically used for capture assays. After the CD34 progenitor cells have been captured, they may be released via an appropriate release mechanism as described herein, such as flowing a buffer containing a release agent that induces oligo cleavage into the flow cell. This may be done in combination with causing mechanical disruption by actuated motion of the surface-attached structures. Other techniques may be utilized to assist in the release process as well, such as electroporation. The released CD34 progenitor cells may be collected separately from the blood, and the blood, now depleted of the CD34 progenitor cells, may be recovered separately.

Example 2—Cell-Free DNA Isolation from Whole Blood

Liquid biopsy entails the isolation and characterization of cells and nucleic acids from biological fluids. Liquid biopsy is among the most exciting areas of new diagnostics development, with a burst of new tests for fetal screening and cancer genotyping. In both contexts, circulating nucleic acids (NAs) promise a minimally invasive method for detecting and monitoring disease. Yet costs and risks associated with the tests as presently offered are substantial. Fetal testing is used by patients to make irreversible decisions, including pregnancy termination; because of poor specificity, circulating fetal deoxyribonucleic acid (DNA) tests are recommended only for screening of high-risk patients. Cancer genotyping may be used to guide the selection of therapies that, when poorly matched to the cancer, may have very low efficacy; as a result, the patient suffers needless costs, side effects, and loss of time that could have been spent with a more effective therapy.

A liquid biopsy involves three general steps: sample collection, analyte purification, and analysis. Sample collection is a simple blood draw. Analysis is the subject of intense investment and development. The middle step—purification—has received relatively little attention. Circulating NAs are present in very low concentrations. Presently, collection and purification require either much hands-on processing or expensive robotic equipment at a specialized Clinical Laboratory Improvement Amendments (CLIA) lab. In particular, column-based purification is laborious and time consuming, while automated, bead-based methods require complex robotic equipment. Special, expensive tubes are used to preserve samples during storage and transit. The complex, multi-step protocols-both automated and manual-create opportunities for sample contamination.

It would be advantageous to improve the reliability of liquid biopsy by improving the sample itself. The ideal extraction method would be: 1) closed, meaning the extraction system is a low-maintenance, affordable instrument that accepts a sealed container of raw sample and furnishes a sealed container of the extracted analyte, with no operator access to the sample in between; 2) purifying and concentrating, meaning the solvent is buffer, the solute is predominantly NA, and the eluted volume is small (~100 µL, a typical molecular analyzer capacity); and 3) rapid and compact, meaning the extraction is performed at point of care, within 30 minutes of sample collection.

Such a system could allow sample collection with standard ethylenediaminetetraacetic acid (EDTA) tubes and on-site purification. CLIA labs could ship small vials of purified, stabilized DNA, ready for analysis using their molecular detection technology of choice. This system could reduce costs for existing tests by simplifying the workflow. It could reduce the cost of studying circulating NAs, and therefore accelerate clinical research and diagnostics development. And it could be a keystone technology for enabling completely point-of-care cell-free DNA (cfDNA) diagnostics.

A flow cell as described herein may be utilized to implement a method of inline NA extraction from whole blood. The flow cell may be utilized to isolate cfDNA from a large sample volume (e.g., greater than 10 mL) by passing it through a small (e.g., ~100 µL) chamber of the flow cell. The surface-attached structures of the flow cell may include a binding agent exhibiting a specific affinity to the cfDNA, such as histone antibodies as may be utilized in chromatin immunoprecipitation (ChIP). In a specific example, the surface-attached structures are impregnated with biotinylated phospholipid (Bio-DOPE), and then surface-treated with streptavidin which binds to the biotinylated histone antibody. Non-specific adsorption (NSA) is suppressed by impregnating nonionic surfactants into the elastomer (e.g., Brij-35, TWEEN®-20 (polysorbate 20, or polyoxyethylene (20) sorbitan monolaurate), surface treating with non-ionic surfactants or lipid treatments (Egg-PC), and/or adsorbing blocking proteins or polyelectrolytes (bovine serum albumin (BSA), poly-L-lysine).

Typical human blood is ~50% cellular material that is denser and larger than cfDNA. To take advantage of this, the flow cell may be operated with the tips of the surface-attached structures pointing down, so that the gap (e.g., 30 µm) between the tips and the opposite surface creates a cell settling region. As the surface-attached structures move, they size-exclude cells into the region below, which process is assisted by gravity.

After the cfDNA has been captured, it may be released via an appropriate release mechanism as described herein, such as one that induces proteolysis (e.g., the protease known as Proteinase K). The flowing of the protease into the flow cell may be done in combination with causing mechanical disruption by actuated motion of the surface-attached structures. Other techniques may be utilized to assist in the release process as well, such as electroporation. Subsequent elution into buffer may produce a pure analyte.

Microfluidic devices have been developed to perform nucleic acid extraction using other techniques such as electrokinesis, but these have been demonstrated only with very small volumes (less than 100 µL of whole blood). By contrast, a flow cell as described herein may process much larger volumes as indicated above. Moreover, the surface-attached structures in the flow cell provide a surface area-to-volume ratio at least as high as that provided by conventional columns, yet are able to prevent or disrupt clogging through actuated movement as described herein. The flow cell is compact and thus may enable superior point-of-care diagnostics. Also, the flow cell enables a fully closed process, thereby reducing risk of contamination. Moreover, use of the flow cell does not destroy the blood that passes through, potentially enabling apheresis-like diagnostics. Because the binding chemistry is modular, the flow cell may be modified to process samples such as urine, bronchoalveolar lavage, sputum, or spinal fluid. It could also be modified to capture other analytes such as circulating tumor cells, stem cells, or pathogens.

Example 3—Pathogen Isolation from Whole Blood

Hospital acquired infection (HAI) that leads to sepsis is deadly, expensive, and increasingly common. Severe sepsis affects more than one million U.S. patients per year; the mortality is ~30% and the cost to the health care system is roughly $20 billion. Rapid anti-microbial treatment is key to improving outcomes, as is identifying the strain of the pathogen. Strain identification reduces costs, improves care, and avoids overuse of antimicrobials.

Techniques for strain identification are rapidly improving, but challenges remain. The traditional method relies exclusively on blood culture (BC). This process takes days. Worse, blood culture suffers poor specificity due to contamination and poor sensitivity because pathogens do not always culture successfully. New molecular techniques from firms like BioFire shorten the time-to-result, but a culture step is still required. Novel techniques are under development that are sensitive enough to sequence pathogens without amplification by culture, but delivering on their promise will require a cost-effective and automated solution for extracting the target molecular analyte from large volumes of blood.

Blood has antimicrobial activity and patients often have circulating antibiotics that reduce BC viability; pathogen purification improves viability, especially when initial pathogen concentration is low. For molecular assays based on polymerase chain reaction (PCR), typical protocols lyse all cells (blood and bacterial), releasing as much as 1000× more human DNA than pathogenic DNA. This results in non-specific amplification, reducing sensitivity of the technique. Such "molecular background" often sets the limit of detection in PCR. It also precludes the use of direct sequencing methods. This background can be eliminated only by purifying the pathogen from blood prior to lysis.

At onset of sepsis, bacterial concentration in blood is low (e.g., 10-100 colony forming units (CFU)/ml in adults, and less than 10 CFU/ml in neonates). A conventional molecular technique might process 1 mL of blood and have a limit of detection of 10-50 CFU/mL. However, the same culture-free molecular analysis of pathogens purified from 10-60 mL would be sensitive enough to monitor bacteremia from the earliest stages of sepsis—or perhaps, even earlier, such that optimally targeted therapy could begin immediately upon diagnosis.

A flow cell as described herein may be utilized to isolate bacteria from a large sample volume such as the above-noted range of 10-60 mL. As in other applications disclosed herein, the surface-attached structures in the flow cell may be moved to provide an anti-clogging functionality. The attached structures of the flow cell may include a binding agent exhibiting a specific affinity to the bacteria, such as histone antibodies as may be utilized in chromatin immunoprecipitation (ChIP). In a specific example, the surface-attached structures are impregnated with biotinylated phospholipid (Bio-DOPE), and then surface-treated with streptavidin which binds to the biotinylated mannose-binding lectin (MBL). Non-specific adsorption (NSA) is suppressed by impregnating nonionic surfactants into the elastomer (e.g., Brij-35, TWEEN®-20 (polysorbate 20, or polyoxyethylene (20) sorbitan monolaurate), surface treating with non-ionic surfactants or lipid treatments (Egg-PC), and/or adsorbing blocking proteins or polyelectrolytes (bovine serum albumin (BSA), poly-L-lysine).

After the bacteria has been captured, a buffer containing an appropriate lysing agent may be introduced into the flow cell behind the blood sample to lyse the bacteria and thereby release its components (including DNA) into a smaller volume of, for example, 100 μL. As in other applications, the lytic-based release process may be performed in combination with causing mechanical disruption by actuated motion of the surface-attached structures. Other techniques may be utilized to assist in the release process as well, such as electroporation.

It will be understood that various aspects or details of the invention may be changed without departing from the scope of the invention. Furthermore, the foregoing description is for the purpose of illustration only, and not for the purpose of limitation—the invention being defined by the claims.

What is claimed is:

1. A flow cell, comprising:
    a chamber enclosing an interior and comprising a fluid inlet, a fluid outlet, and an inside surface facing the interior;
    a plurality of surface-attached structures attached to the inside surface at a plurality of respective attachment sites and extending into the interior therefrom, each surface-attached structure comprising a flexible body and a metallic component disposed on or in the body, and
    a driver configured for applying a magnetic or electric field to the interior of the flow cell to actuate movement of the surface-attached structures;
    wherein application of a magnetic or electric field actuates the surface-attached structure into movement relative to the corresponding attachment site.

2. The flow cell of claim 1, further comprising a binding agent configured for binding to a target present in the interior, wherein the binding agent is selected from the group consisting of:
    a binding agent disposed on or integrated with an outer surface of at least some of the surface-attached structures;
    a binding agent disposed on or integrated with the inside surface; and
    both of the foregoing.

3. The flow cell of claim 2, wherein at least one of the target and the binding agent is selected from the group consisting of: a biological cell; an intracellular component; a microbe; a pathogen; a carcinogen; an antigen; a hapten; an antibody; a toxin; a drug; a steroid; a vitamin; a biopolymer a biological compound; a hormone; an allergen; a pesticide; a chemical compound; a molecule; a chemical element; a fragment, particle, or partial structure of any of the foregoing; and a binding partner of any of the foregoing.

4. The flow cell of claim 2, wherein the outer surfaces of the surface-attached structures, or the inside surface, or both the outer surfaces and the inside surface, are chemically pacified to suppress non-specific binding.

5. The flow cell of claim 2, wherein the flow cell has an interior volume on the order of microliters or nanoliters.

6. The flow cell of claim 2, wherein the chamber comprises an optically transparent wall exposed to at least a portion of the interior.

7. The flow cell of claim 2, wherein:
    each surface-attached structure comprises a fixed end at the attachment site, a free end, a length from the fixed end to the free end, and a cross-section orthogonal to the length and having a characteristic dimension; and
    the length, or the characteristic dimension, or both the length and the characteristic dimension, are on the order of micrometers or nanometers.

8. The flow cell of claim 2, wherein the surface-attached structures have a geometry selected from the group consisting of: a cylinder; a polygon; a shape having both polygonal and rounded features; a rounded cross-section; a circular cross-section; an ovular cross-section; an elliptical cross-section; a polygonal cross-section; a square cross-section; a rectangular cross-section; a triangular shape selected from the group consisting of circular, ovular, square, rectangular, and triangular cross-section; and an irregular cross-section.

9. The flow cell of claim 2, wherein the plurality of surface-attached structures has an inter-structure spacing on the order of micrometers or nanometers.

10. The flow cell of claim 9, wherein the inter-structure spacing is selected to perform size exclusion separation or filtration on a target-containing sample flowing through the chamber.

11. The flow cell of claim 2, wherein:
    the inside surface is a first inside surface, and the chamber further comprises a second inside surface spaced from the first inside surface such that the interior is between the first inside surface and the second inside surface; and
    each surface-attached structure has a structure length, the interior comprises a structure-free region between the surface-attached structures and the second inside surface.

12. The flow cell of claim 2, wherein:
    the inside surface is a first inside surface, and the chamber further comprises a second inside surface spaced from the first inside surface such that the interior is between the first inside surface and the second inside surface; and
    the first inside surface and the surface-attached structures are above the second inside surface, or the first inside surface and the surface-attached structures are below the second inside surface.

13. The flow cell of claim 2, wherein:
    the inside surface is a first inside surface, and the chamber further comprises a second inside surface spaced from the first inside surface such that the interior is between the first inside surface and the second inside surface;
    the plurality of surface-attached structures is a plurality of first surface-attached structures attached to the first inside surface, and further comprising a plurality of second surface-attached structures attached to the second inside surface at a plurality of respective attachment sites and extending into the interior toward the first surface-attached structures; and
    the interior comprises a structure-free region between the first surface-attached structures and the second surface-attached structures.

14. The flow cell of claim 2, wherein the body of each surface-attached structure has a composition selected from the group consisting of: an elastomeric material, and polydimethylsiloxane (PDMS).

15. The flow cell of claim 2, wherein the metallic component has a composition selected from the group consisting of: a ferromagnetic material, iron, a magnetic iron alloy, nickel, a magnetic nickel alloy, cobalt, a magnetic cobalt alloy, copper, aluminum, gold, and silver.

16. A flow cell, comprising:
    a plurality of flow cell units, each flow cell unit comprising a chamber and a plurality of surface-attached structures according to claim 1, wherein the plurality of flow cell units has a configuration selected from the group consisting of:

the flow cell units are stacked in parallel; and the flow cell units are arranged in series such that the fluid inlet or the fluid outlet of each flow cell unit communicates with the fluid inlet or the fluid outlet of at least one other flow cell unit.

17. The flow cell of claim 16, wherein the flow cell units are stacked in parallel, and further comprising a common fluid port communicating with the fluid inlets or the fluid outlets of the flow cell units.

18. A target extraction system, comprising:

the flow cell of claim 2; and a driver configured for applying a magnetic or electric field to the interior of the flow cell to actuate movement of the surface-attached structures.

19. The target extraction system of claim 18, wherein the driver is configured for moving relative to the flow cell.

20. The target extraction system of claim 18, wherein the driver comprises one or more permanent magnets, electromagnets, or a combination of one or more permanent magnets and one or more electromagnets.

21. The flow cell of claim 1, further comprising:

a binding agent disposed on or integrated with an outer surface of at least some of the surface-attached structures, the binding agent having a specific affinity for a target;

a sample comprising the target, wherein the sample is in contact with the plurality of surface-attached structures; and target bound to the binding agent;

wherein the surface-attached structures are moving relative to the corresponding attachment site and the target consists of a biochemical compound.

22. The flow cell of claim 21, wherein the sample comprising the target comprises a bodily fluid.

23. The flow cell of claim 21, wherein the binding agent and target is selected from the group consisting of the following binding agent-target combinations: antibody-antigen, antibody-hapten, hormone-hormone receptor, lectin-carbohydrate, enzyme-enzyme inhibitor, enzyme-cofactor, biotin-avidin, biotin-streptavidin, ligand-ligand receptor, protein-immunoglobulin, and nucleic acid-complementary nucleic acid.

24. The flow cell of claim 2, wherein the binding agent comprises a biological cell or an intracellular component.

* * * * *